United States Patent
Chackalamannil et al.

(10) Patent No.: US 7,037,920 B2
(45) Date of Patent: May 2, 2006

(54) SUBSTITUTED TRICYCLIC HIMBACINE DERIVATIVES THAT ARE USEFUL AS THROMBIN RECEPTOR ANTAGONISTS

(75) Inventors: Samuel Chackalamannil, East Brunswick, NJ (US); Mariappan V. Chelliah, Edison, NJ (US); Martin C. Clasby, Plainsboro, NJ (US); Yan Xia, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 214 days.

(21) Appl. No.: 10/271,715

(22) Filed: Oct. 16, 2002

(65) Prior Publication Data

US 2003/0203927 A1 Oct. 30, 2003

Related U.S. Application Data

(60) Provisional application No. 60/330,359, filed on Oct. 18, 2001.

(51) Int. Cl.
*A61K 31/4355* (2006.01)
*C07D 515/04* (2006.01)

(52) U.S. Cl. .................. 514/291; 514/339; 546/80; 546/284.1

(58) Field of Classification Search .............. 546/284.1, 546/80; 514/339, 291
See application file for complete search history.

(56) References Cited

U.S. PATENT DOCUMENTS

| 5,716,952 | A   |   | 2/1998  | WoldeMussie et al. |         |
|-----------|-----|---|---------|--------------------|---------|
| 6,063,847 | A   | * | 5/2000  | Chackalamannil et al. | 524/297 |
| 6,326,380 | B1  | * | 12/2001 | Chackalamannil et al. | 514/311 |

FOREIGN PATENT DOCUMENTS

| EP | 1 138 679 | 10/2001 |
| WO | 94/03479  | 2/1994  |
| WO | 01/96330  | 12/2001 |

OTHER PUBLICATIONS

Bernatowicz et al, *J. Med. Chem.*, 39 (1996), p. 4879–4887.
Chackalamannil et al, *J. Am. Chem. Soc.*, 118 (1996), p. 9812–9813.
Pertwee, *Curr. Med. Chem.*, 6 (1999), p. 635–664.
Natarajan et al, *Int. J. Peptide Protein Res.*, 45 (1995), p. 145–151.
Lowry et al, *J. Biol. Chem.*, 193 (1951), 265–275.
Ahn et al, *Mol. Pharmacol.*, 51 (1997), p. 350–356.
Bednar et al, *Thromb. Res.*, 77 (1995), p. 453–463.
Even–Ram et al, *Nature Med.*, 4, (8) (1988), p. 909–914.
Malaska et al, *Bioorganic & Medicinal Chemistry Letters*, 5 (1) (1995), 61–66.
Takadoi et al, *Tetrahedron Letters*, 40 (1999), 3399–3402.
Doller et al, *Bioorganic & Medicinal Chemistry Letters*, 9 (1999), 901–906.

* cited by examiner

*Primary Examiner*—Rita Desai
(74) *Attorney, Agent, or Firm*—Gerard E. Reinhardt; William Y. Lee

(57) ABSTRACT

Heterocyclic-substituted tricyclics of the formula

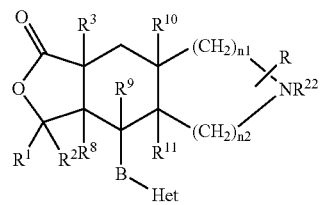

or a pharmaceutically acceptable salts thereof, wherein:
  $n_1$ and $n_2$ are independently 0–2;
  Het is an optionally substituted mono-, bi- or tricyclic heteroaromatic group;
  B is alkyl or optionally substituted alkenyl;
  $R^{22}$ is —$COR^{23}$ or a carboxy, sulfinyl, sulfonyl, sulfonamide or amino acid derivative;
  $R^{23}$ is haloalkyl; alkenyl; haloalkenyl; alkynyl; optionally substituted cycloalkyl; cycloalkyl-alkyl; aryl; arylalkyl; heteroaryl; heterocycloalkyl; or —COOH and/or —$SO_3H$ substituted alkyl;
  $R^1$, $R^2$, $R^3$, $R^9$, $R^{10}$ and $R^{11}$ are as defined in the specification;
are disclosed, as well as pharmaceutical compositions containing them and a method of treating diseases associated with thrombosis, atherosclerosis, restenosis, hypertension, angina pectoris, arrhythmia, heart failure, and cancer by administering said compounds.

15 Claims, No Drawings

SUBSTITUTED TRICYCLIC HIMBACINE DERIVATIVES THAT ARE USEFUL AS THROMBIN RECEPTOR ANTAGONISTS

CROSS REFERENCE TO RELATED APPLICATION

This application claims the benefit of U.S. Provisional Application No. 60/330,359, filed Oct. 18, 2001.

BACKGROUND OF THE INVENTION

Thrombin is known to have a variety of activities in different cell types and thrombin receptors are known to be present in such cell types as human platelets, vascular smooth muscle cells, endothelial cells and fibroblasts. It is therefore expected that thrombin receptor antagonists will be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, *J. Med. Chem.*, 39 (1996), p. 4879–4887, tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cinnamoyl-p-fluoroPhe-p-guanidinoPhe-Leu-Arg-Arg-$NH_2$. Peptide thrombin receptor anatgonists are also disclosed in WO 94/03479, published Feb. 17, 1994.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation. As such, a selective $CB_2$ receptor binding agent is expected to have therapeutic utility in the control of diseases associated with rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (R. G. Pertwee, *Curr. Med. Chem.* 6(8), (1999), 635).

Himbacine, a piperidine alkaloid of the formula

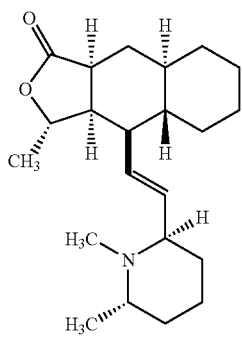

has been identified as a muscarinic receptor antagonist. The total synthesis of (+)-himbacine is disclosed in Chackalamannil et al, *J. Am. Chem. Soc.*, 118 (1996), p. 9812–9813.

SUMMARY OF THE INVENTION

The present invention relates to thrombin receptor antagonists represented by the formula I

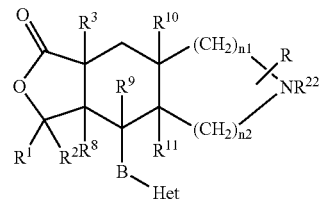

or a pharmaceutically acceptable salt thereof, wherein:

R is 1 to 3 substituents independently selected from the group consisting of H, $C_1$–$C_6$ alkyl, halogen, hydroxy, amino, ($C_1$–$C_6$)alkyl-amino, ($C_1$–$C_6$)-dialkylamino, ($C_1$–$C_6$)alkoxy, —$COR^{16}$, —$COOR^{17}$, —$SOR^{16}$, —$SO_2R^{16}$, —$SO_2NR^{17}R^{18}$, —$NR^{17}SO_2R^{16}$, —$NR^{16}COR^{16a}$, —$NR^{16}COOR^{16a}$, —$NR^{16}CONR^4R^5$, fluoro-($C_1$–$C_6$)alkyl, difluoro($C_1$–$C_6$)alkyl, trifluoro($C_1$–$C_6$)alkyl, $C_3$–$C_6$ cycloalkyl, aryl($C_1$–$C_6$)alkyl, hydroxy($C_1$–$C_6$)alkyl, amino-($C_1$–$C_6$)-alkyl, aryl and thio($C_1$–$C_6$)alkyl;

$R^1$ and $R^2$ are independently selected from the group consisting of H, $C_1$–$C_6$ alkyl, fluoro($C_1$–$C_6$)alkyl, difluoro ($C_1$–$C_6$)alkyl, trifluoro-($C_1$–$C_6$)alkyl, $C_3$–$C_6$ cycloalkyl, $C_2$–$C_6$ alkenyl, aryl($C_1$–$C_6$)alkyl, hydroxy-($C_1$–$C_6$)alkyl, amino($C_1$–$C_6$)alkyl, aryl and thio($C_1$–$C_6$)alkyl; or $R^1$ and $R^2$ together form an =O group;

$R^3$ is H, hydroxy, $C_1$–$C_6$alkoxy, aryloxy, aryl($C_1$–$C_6$) alkyloxy, heteroaryloxy, heteroaryl($C_1$–$C_6$)alkyloxy, ($C_3$–$C_6$)cycloalkyloxy, —$SOR^{16}$, —$SO_2R^{17}$, —$SO_2NR^{18}R^{19}$, —$SR^{18}$, —$SO_3H$, —$C(O)OR^{17}$, —$C(O)NR^{18}R^{19}$, —$OC(O)R^{32}$, —$OC(O)NR^{33}R^{34}$, —$(CR^{33}R^{34})_n$ $OR^{32}$, —$NR^4R^5$, —$NR^{33}COOR^{32}$, —$NR^{33}COR^{32}$, —$NR^{33}S(O)_2R^{32}$, —$NR^{33}CONR^{33}R^{34}$, —$NR^{33}S(O)_2$ $NR^{33}R^{34}$, —$(CR^{33}R^{34})_nNR^4R^5$, —$(CR^{33}R^{34})_n$ $NR^{33}COOR^{32}$, —$(CR^{33}R^{34})_nNR^{33}COR^{32}$, —$(CR^{33}R^{34})_n$ $NR^{33}S(O)_2R^{32}$, —$(CR^{33}R^{34})_nNR^{33}CONR^{33}R^{34}$, —$(CR^{33}R^{34})_nNR^{33}S(O)_2NR^{33}R^{34}$, ($C_1$–$C_6$)alkyl, halogen, $C_3$–$C_6$ cycloalkyl, $C_2$–$C_6$ alkenyl, —CN, aryl, heteroaryl, heterocycloalkyl, —$P(O)(OR^7)_2$ or ($C_1$–$C_6$)alkyl substituted by 1 to 3 substituents independently selected from the group consisting of halogen, —OH, —$NH_2$, aryl, —COOH, —$SO_3H$, thio and ($C_1$–$C_6$)alkylthio;

n is 1, 2, 3 or 4;

n1 and n2 are independently 0–3, provided both are not 0;

Het is a mono-, bi- or tricyclic heteroaromatic group of 5 to 14 atoms comprised of 1 to 13 carbon atoms and 1 to 4 heteroatoms independently selected from the group consisting of N, O and S, wherein a ring nitrogen can form an N-oxide or a quaternary group with a $C_1$–$C_4$ alkyl group, wherein Het is attached to B by a carbon atom ring member, and wherein the Het group is substituted by 1 to 4 substituents, W, independently selected from the group consisting of $C_1$–$C_6$ alkyl;

—$NR^4R^5$; —$NHCOR^{26}$; —$NHSO_2R^{16}$;

$R^{21}$-aryl; aryl wherein adjacent carbons form a ring with a methylenedioxy group; and $R^{21}$-heteroaryl;

$R^4$ and $R^5$ are independently selected from the group consisting of H, $C_1$–$C_6$ alkyl, phenyl, benzyl and $C_3$–$C_6$ cycloalkyl, or $R^4$ and $R^5$ together are —$(CH_2)_3$—, —$(CH_2)_4$—, —$(CH_2)_5$— or —$(CH_2)_2NR^7$—$(CH_2)_2$— and form a ring with the nitrogen to which they are attached;

$R^7$ is H or $(C_1-C_6)$alkyl;

$R^8$, $R^{10}$ and $R^{11}$ are independently selected from the group consisting of $R^1$ and —$OR^1$;

$R^9$ is H, OH, —$NR^4R^5$, $C_1-C_6$alkoxy, halogen or halo $(C_1-C_6)$alkyl;

B is —$(CH_2)n_3$— or cis or trans —$(CH_2)n_4CR^{12}$=$CR^{12a}$ $(CH_2)n_5$, wherein $n_3$ is 0–5, $n_4$ and $n_5$ are independently 0–2, and $R^{12}$ and $R^{12a}$ are independently selected from the group consisting of H, $C_1-C_6$ alkyl and halogen;

$R^{16}$ and $R^{16a}$ are independently selected from the group consisting of $C_1-C_6$ alkyl, phenyl and benzyl;

$R^{17}$, $R^{18}$ and $R^{19}$ are independently selected from the group consisting of H, $C_1-C_6$alkyl, phenyl and benzyl;

$R^{21}$ is 1 to 3 substituents independently selected from the group consisting of H, —$CF_3$, —$OCF_3$, halogen, —$NO_2$, —CN, $C_1-C_6$ alkyl, $C_1-C_6$ alkoxy, —$NH_2$, $(C_1-C_6)$-alkylamino, di-$((C_1-C_6)$alkyl)amino, amino$(C_1-C_6)$alkyl, $(C_1-C_6)$-alkylamino$(C_1-C_6)$alkyl, di-$((C_1-C_6)$alkyl)-amino$(C_1-C_6)$alkyl, hydroxy-$(C_1-C_6)$alkyl, —$COOR^{17}$, —$COR^{17}$, —$CONR^{24}R^{25}$, —$NHCOR^{16}$, —$NHSO_2R^{16}$, —$NHSO_2CH_2CF_3$, —$SO_2NR^{24}R^{25}$, —$NR^{29}C(O)NR^{24}R^{25}$, —$SO_2R^{30}$, —$P(O)(OR^{29})_2$, aryl, aryl$(C_1-C_6)$alkyl, heteroaryl, heterocycloalkyl, and —$CR^{29}$(=$NOR^{28}$);

$R^{22}$ is —$COR^{23}$, —$S(O)R^{31}$, —$S(O)_2R^{31}$, —$SO_2NR^{24}R^{25}$ or —$COOR^{27}$;

$R^{23}$ is halo$(C_1-C_6)$alkyl; $C_2-C_6$ alkenyl; halo$(C_2-C_6)$ alkenyl; $C_2-C_6$ alkynyl; $C_3-C_7$-cycloalkyl; $(C_3-C_7)$ cycloalkyl$(C_1-C_6)$alkyl; $(C_3-C_7)$cycloalkyl substituted by 1 to 3 substituents selected from the group consisting of halo, $(C_1-C_3)$alkoxy$(C_1-C_3)$alkyl, hydroxy and $C_1-C_6$ alkoxy; aryl; aryl$(C_2-C_6)$alkyl; heteroaryl; heterocycloalkyl; $(C_1-C_6)$alkyl substituted by 1–3 substituents independently selected from —COOH and —$SO_3H$; or

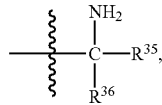

wherein $R^{35}$ and $R^{36}$ are independently selected from the group consisting of H, alkyl, or $R^{37}$-substituted $C_1-C_6$ alkyl, wherein $R^{37}$ is selected from the group consisting of HO—, HS—, $CH_2S$—, —$NH_2$, phenyl, p-hydroxyphenyl and indolyl;

$R^{24}$ and $R^{25}$ are independently selected form the group consisting of H, $C_1-C_6$ alkyl, halo$(C_1-C_6)$alkyl, $C_2-C_6$ alkenyl, halo$(C_2-C_6)$alkyl, $C_2-C_6$ alkynyl, aryl, aryl-$(C_1-C_6)$alkyl, $C_{3-C_7}$-cycloalkyl, halo$(C_3-C_7)$cycloalkyl, $(C_1-C_3)$alkoxy$(C_1-C_3)$-alkyl, hydroxy and $C_1-C_6$ alkoxy;

$R^{26}$ is $C_3-C_7$-cycloalkyl, aryl, aryl-$(C_1-C_6)$alkyl, heteroaryl, heteroaryl-$(C_1-C_6)$alkyl or $(C_1-C_6)$alkylamino;

$R^{27}$ is $C_1-C_6$alkyl, phenyl, benzyl, $(C_1-C_3)$alkoxy $(C_1-C_3)$-alkyl, $(C_3-C_7)$-cycloalkyl, carboxy$(C_1-C_6)$alkyl, sulfo$(C_1-C_6)$alkyl, or $(C_1-C_6)$alkyl substituted by $NR^{18}R^{19}$ and carboxy;

$R^{28}$ is H, $C_1-C_6$ alkyl, phenyl, benzyl or $(C_1-C_3)$alkoxy $(C_1-C_3)$alkyl;

$R^{29}$ and $R^{30}$ are independently selected from the group consisting of H and $C_1-C_6$ alkyl;

$R^{31}$ is $(C_1-C_6)$alkyl; halo$(C_1-C_6)$alkyl; $C_2-C_6$ alkenyl; halo$(C_2-C_6)$alkyl; $C_2-C_6$ alkynyl; $C_3-C_7$-cycloalkyl; $(C_3-C_7)$cycloalkyl substituted by 1 to 3 substituents selected from the group consisting of halo, $(C_1-C_3)$alkoxy$(C_1-C_3)$ alkyl, hydroxy and $C_1-C_6$ alkoxy; aryl; aryl$(C_1-C_6)$alkyl; heteroaryl; heterocycloalkyl; $(C_1-C_6)$alkyl substituted by 1–3 substituents independently selected from —COOH and —$SO_3H$; or $(C_1-C_6)$alkoxy;

$R^{32}$ is $R^{35}$—$(C_1-C_6)$alkyl, $R^{35}$—$(C_3-C_7)$cycloalkyl, $R^{35}$—$(C_2-C_6)$alkenyl, $R^{35}$—$(C_2-C_6)$-alkynyl or $R^{35}$-aryl, wherein $R^{35}$ is 1 or 2 substituents independently selected from the group consisting of H, —COOH, —$NH_2$, —$SO_3H$, =O and =$NOR^{28}$; and $R^{33}$ and $R^{34}$ are independently selected from the group consisting of H, $(C_1-C_6)$alkyl and $C_3-C_7$-cycloalkyl.

This invention also relates to a method of using a compound of formula I in the treatment of thrombosis, atherosclerosis, restenosis, platelet aggregation, coagulation, cancer, inflammatory diseases or respiratory diseases, comprising administering a compound of formula I to a mammal in need of such treatment. In particular, the present invention relates to a method of using a compound of formula I in the treatment of thrombosis, atherosclerosis, restenosis, hypertension, angina pectoris, arrhythmia, heart failure, myocardial infarction, glomerulonephritis, thrombotic stroke, thromboembolytic stroke, peripheral vascular diseases, cerebral ischemia, cancer, rheumatoid arthritis, systemic lupus erythematosus, multiple sclerosis, diabetes, osteoporosis, renal ischemia, cerebral stroke, nephritis, inflammatory disorders of the lungs and gastrointestinal tract, reversible airway obstruction, chronic asthma or bronchitis. It is contemplated that a compound of this invention may be useful in simultaneously treating more than one of the diseases listed.

In another aspect, the invention relates to a pharmaceutical composition comprising at least one compound of formula I in a pharmaceutically acceptable carrier.

In yet another aspect, the invention relates to the novel compounds represented by the structural formula

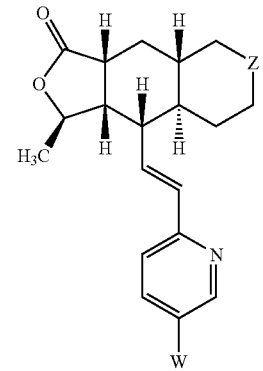

wherein W and Z are as defined in the following table:

| W | Z |
|---|---|
| ![benzene with CF3] | —S— |
| ![benzene with CF3] | —S(O)— |

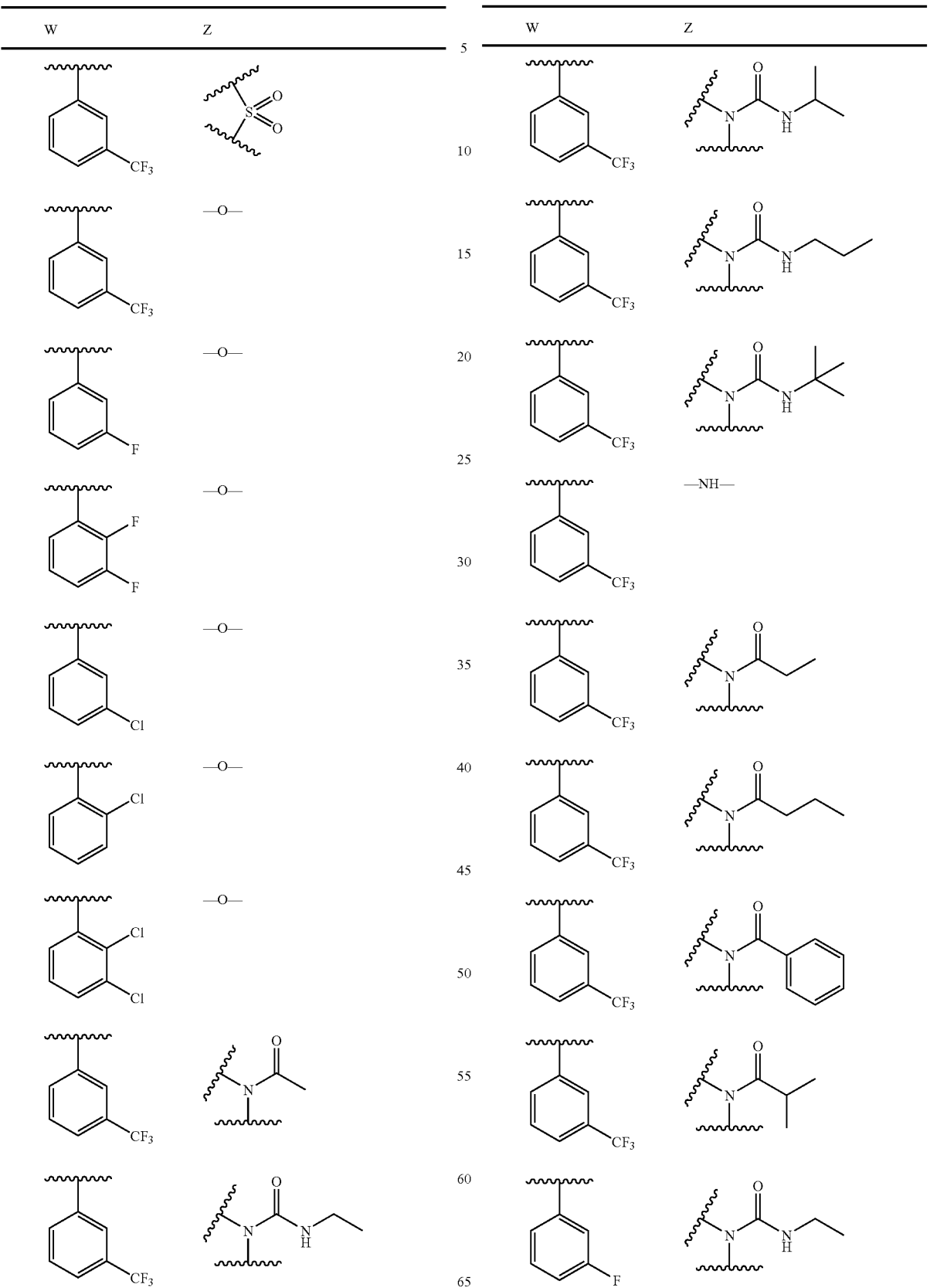

| W | Z |
|---|---|
| [2-fluorophenyl] | [N-ethyl urea: -N(-)C(=O)NH-ethyl] |
| [3-fluorophenyl] | [N-carbamoyl: -N(-)C(=O)NH₂] |
| [3-fluorophenyl] | [N-phenylacetyl: -N(-)C(=O)CH₂-phenyl] |
| [2,3-difluorophenyl] | [N-ethyl urea: -N(-)C(=O)NH-ethyl] |
| [3-trifluoromethylphenyl] | —N(CH₃)— |

DETAILED DESCRIPTION

The present invention relates to substituted tricyclic himbacine derivatives having one or more of anti-thrombotic, anti-platelet aggregation, antiatherosclerotic, antirestenotic and anti-coagulant activity. Thrombosis-related diseases treated by the compounds of this invention include thrombosis, atherosclerosis, restenosis, hypertension, angina pectoris, arrhythmia, heart failure, myocardial infarction, glomerulonephritis, thrombotic and thromboembolytic stroke, peripheral vascular diseases, other cardiovascular diseases, cerebral ischemia, inflammatory disorders, neuro-degenerative diseases and cancer, as well as other disorders in which thrombin and its receptor play a pathological role. Thrombin receptor antagonists are also known as protease activated receptor (PAR) antagonists.

The compounds of the invention also bind to cannabinoid (CB2) receptors and are useful in the treatment of inflammatory diseases or respiratory diseases such as one or more of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis.

Preferred definitions of the variables in the structure of formula I are as follows:

The sum of n1 and n2 is preferably 2–3, more preferably 3. Especially preferred are compounds of formula I wherein n1 is 1 and n2 is 2, or n1 is 0 and n2 is 3.

R is preferably 1 substituent selected from the group consisting of H, $C_1$–$C_6$ alkyl, halogen, hydroxy, amino and ($C_1$–$C_6$)alkoxy.

$R^1$ and $R^2$ are preferably independently selected from the group consisting of H and $C_1$–$C_6$ alkyl; more preferably, $R^1$ is $C_1$–$C_6$ alkyl and $R^2$ is H.

$R^3$ is preferably H, hydroxy, $C_1$–$C_6$alkoxy, halogen, $C_3$–$C_6$ cycloalkyl, —CN, ($C_1$–$C_6$)alkyl, —COOR$^{17}$ or —NR$^4$R$^5$, more preferably H, hydroxy or ($C_1$–$C_6$)alkyl.

Het is preferably pyridyl or quinolyl attached to B by a carbon atom ring member, and substituted by 1 to 4 substituents selected from W.

W is preferably selected from —NR$^4$R$^5$, —NHCOR$^{26}$, —NHSO$_2$R$^{16}$, R$^{21}$-aryl and heteroaryl.

$R^4$ and $R^5$ are preferably independently selected from the group consisting of H, $C_1$–$C_6$ alkyl and $C_3$–$C_6$ cycloalkyl, or $R^4$ and $R^5$ together are —(CH$_2$)$_3$—, —(CH$_2$)$_4$— or —(CH$_2$)$_5$— and form a ring with the nitrogen to which they are attached.

$R^8$, $R^{10}$ and $R^{11}$ are preferably H or ($C_1$–$C_6$)alkyl.

$R^9$ is preferably H, OH or $C_1$–$C_6$alkoxy.

B is preferably trans —CH=CH—.

$R^{16}$ is preferably $C_1$–$C_6$ alkyl.

$R^{21}$ is preferably 1 to 3 substituents independently selected from the group consisting of H, —CF$_3$, —OCF$_3$, halogen, —CN, $C_1$–$C_6$ alkyl, $C_1$–$C_6$ alkoxy, —NH$_2$ and —CR$^{29}$(=NOR$^{28}$).

$R^{22}$ is preferably —COR$^{23}$, —S(O)$_2$R$^{31}$ or —COOR$^{27}$.

$R^{23}$ is preferably $C_3$–$C_7$-cycloalkyl; ($C_3$–$C_7$)cyclo-alkyl substituted by 1 to 3 substituents selected from the group consisting of halo, ($C_1$–$C_3$)alkoxy($C_1$–$C_3$)alkyl, hydroxy and $C_1$–$C_6$ alkoxy; ($C_3$–$C_7$)cycloalkyl($C_1$–$C_6$)alkyl; aryl; and aryl($C_2$–$C_6$)alkyl. More preferably, $R^{23}$ is $C_3$–$C_7$-cycloalkyl; ($C_3$–$C_7$)cycloalkyl($C_1$–$C_6$)alkyl or aryl-($C_2$–$C_6$) alkyl, especially cyclopropyl, cyclopropylmethyl, and benzyl.

$R^{27}$ is preferably $C_1$–$C_6$alkyl, phenyl, benzyl, ($C_1$–$C_3$) alkoxy($C_1$–$C_3$)-alkyl, or ($C_3$–$C_7$)-cycloalkyl.

$R^{28}$ is preferably H or $C_1$–$C_6$ alkyl.

$R^{31}$ is preferably ($C_1$–$C_6$)alkyl, $C_3$–$C_7$-cycloalkyl, aryl or aryl($C_1$–$C_6$)alkyl, more preferably ($C_1$–$C_6$)alkyl or aryl ($C_1$–$C_6$)alkyl, especially ($C_1$–$C_6$)alkyl or benzyl.

Unless otherwise defined, the term "alkyl" or "lower alkyl" means straight or branched alkyl chains of 1 to 6 carbon atoms and "alkoxy" similarly refers to alkoxy groups having 1 to 6 carbon atoms.

Fluoroalkyl, difluoroalkyl and trifluoroalkyl mean alkyl chains wherein the terminal carbon is substituted by 1, 2 or 3 fluoroatoms, e.g., —CF$_3$, —CH$_2$CF$_3$, —CH$_2$CHF$_2$ or —CH$_2$CH$_2$F. Haloalkyl means an alkyl chain substituted by 1 to 3 halo atoms.

"Alkenyl" means straight or branched carbon chains of 1 to 6 carbon atoms having one or more double bonds in the chain, conjugated or unconjugated. Similarly, "alkynyl" means straight or branched carbon chains of 1 to 6 carbon atoms having one or more triple bonds in the chain. Where an alkyl, alkenyl or alkynyl chain joins two other variables and is therefore bivalent, the terms alkylene, alkenylene and alkynylene are used. Haloalkenyl means an alkenyl chain substituted by 1 to 3 halo atoms.

"Cycloalkyl" means a saturated carbon ring of 3 to 6 carbon atoms, while "cycloalkylene" refers to a corresponding bivalent ring, wherein the points of attachment to other groups include all positional and stereoisomers. Halocycloalkyl means a cycloalkyl ring substituted by 1 to 3 halo atoms.

"Heterocycloalkyl" as a substituent on Het means saturated rings of 4 to 7 atoms comprised of 3 to 4 carbon atoms and 1 to 3 heteroatoms selected from the group consisting of —O—, —S— and —NR$^7$-joined to the rest of the molecule through a carbon atom. Examples of heterocyclo-alkyl groups are 2-azetidinyl, 2-pyrrolidinyl, tetrahydrothiophen-2-yl, tetrahydro-2-furanyl, 4-piperidinyl, 2-piperazinyl, tetrahydro-4-pyranyl, 2-morpholinyl and 2-thiomorpholinyl.

"Halogen" refers to fluorine, chlorine, bromine or iodine radicals.

When $R^4$ and $R^5$ join to form a ring with the nitrogen to which they are attached, the rings formed are 1-pyrrolidinyl, 1-piperidinyl and 1-piperazinyl, wherein the piperazinyl ring may also be substituted at the 4-position nitrogen by a group $R^7$.

"Dihydroxy($C_1$–$C_6$)alkyl" refers to an alkyl chain substituted by two hydroxy groups on two different carbon atoms.

"Aryl" means phenyl, naphthyl, indenyl, tetrahydronaphthyl or indanyl.

"Heteroaryl" means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included, as well as compounds wherein a ring nitrogen is substituted by a $C_1$–$C_4$ alkyl group to form a quaternary amine. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1, 5 or 1,7), imidazopyridyl, pyrido[2,3]imidazolyl, pyridopyrimidinyl and 7-azaindolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 1-pyridyl, 2-pyridyl, 3-pyridyl and 4-pyridyl. W-substituted heteroaryl refers to such groups wherein substitutable ring carbon atoms have a substituent as defined above, or where adjacent carbon atoms form a ring with an alkylene group or a methylenedioxy group.

The term "Het" is exemplified by the single ring, bicyclic and benzofused heteroaryl groups as defined immediately above, as well as tricyclic groups such as benzoquinolinyl (e.g., 1,4 or 7,8) or phenanthrolinyl (e.g., 1,7; 1,10; or 4,7). Het groups are joined to group B by a carbon ring member, e.g., Het is 2-pyridyl, 3-pyridyl or 2-quinolyl.

Examples of heteroaryl groups wherein adjacent carbon atoms form a ring with an alkylene group are 2,3-cyclopentenopyridine, 2,3-cyclohexenopyridine and 2,3-cycloheptenopyridine.

When $R^{22}$ is —COR$^{23}$ and $R^{23}$ is

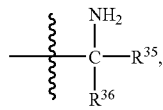

this group is an acyl radical of an amino acid.

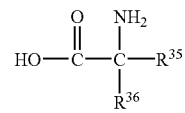

is a naturally occurring amino acid selected from alanine, glycine, valine, leucine, isoleucine, phenylalanine, trytophan, methionine, serine, threonine, cysteine, cystine, or tyrosine.

The above statements, wherein, for example, $R^4$ and $R^5$ are said to be independently selected from a group of substituents, means that $R^4$ and $R^5$ are independently selected, but also that where an $R^4$ or $R^5$ variable occurs more than once in a molecule, those occurrences are independently selected. Those skilled in the art will recognize that the size and nature of the substituent(s) will affect the number of substituents which can be present.

Compounds of the invention have at least one asymmetrical carbon atom and therefore all isomers, including diastereomers and rotational isomers are contemplated as being part of this invention. The invention includes (+)- and (−)-isomers in both pure form and in admixture, including racemic mixtures. Isomers can be prepared using conventional techniques, either by reacting optically pure or optically enriched starting materials or by separating isomers of a compound of formula I.

Typical preferred compounds of the present invention have the following stereochemistry:

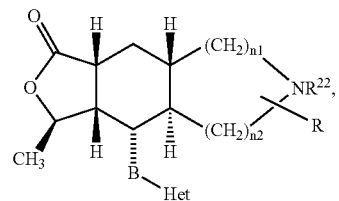

with compounds having that absolute stereochemistry being more preferred.

Those skilled in the art will appreciate that for some compounds of formula I, one isomer will show greater pharmacological activity than other isomers.

Compounds of the invention with a basic group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, lithium, gold and silver salts. Also included are salts formed with pharmaceutically acceptable amines such as ammonia, alkyl amines, hydroxyalkylamines, N-methylglucamine and the like.

Compounds of the present invention are generally prepared by processes known in the art, for example by the processes described below. In the general procedures and examples provided below, the following abbreviations are used: Et is ethyl, Me is methyl, Bn is benzyl, Ac is acetyl, AcOH is acetic acid, THF is tetrahydrofuran, DMF is dimethylformamide, rt is room temperature, Davis reagent is (1S)-(+)-(10-camphorsulfonyl)-oxaziridine, LHMDS is lithium bis(trimethylsilyl)amide, 4-dimethylaminopyridine is DMAP, 1,8-diazabicyclo[5.4.0]undec-7-ene is DBU, 1,3-dicyclohexylcarbodiimide is DCC, and trimethylsilyl iodide is TMSI.

Compounds of formula I-A, wherein B is —CH=CH—, Het is W-substituted pyridyl, R, $R^1$, $R^3$, $R^8$, $R^9$, $R^{10}$ and $R^{11}$ are each hydrogen, $R^2$ is methyl, and $R^{22}$ is —$CO_2Et$ can be prepared as shown in Scheme 1:

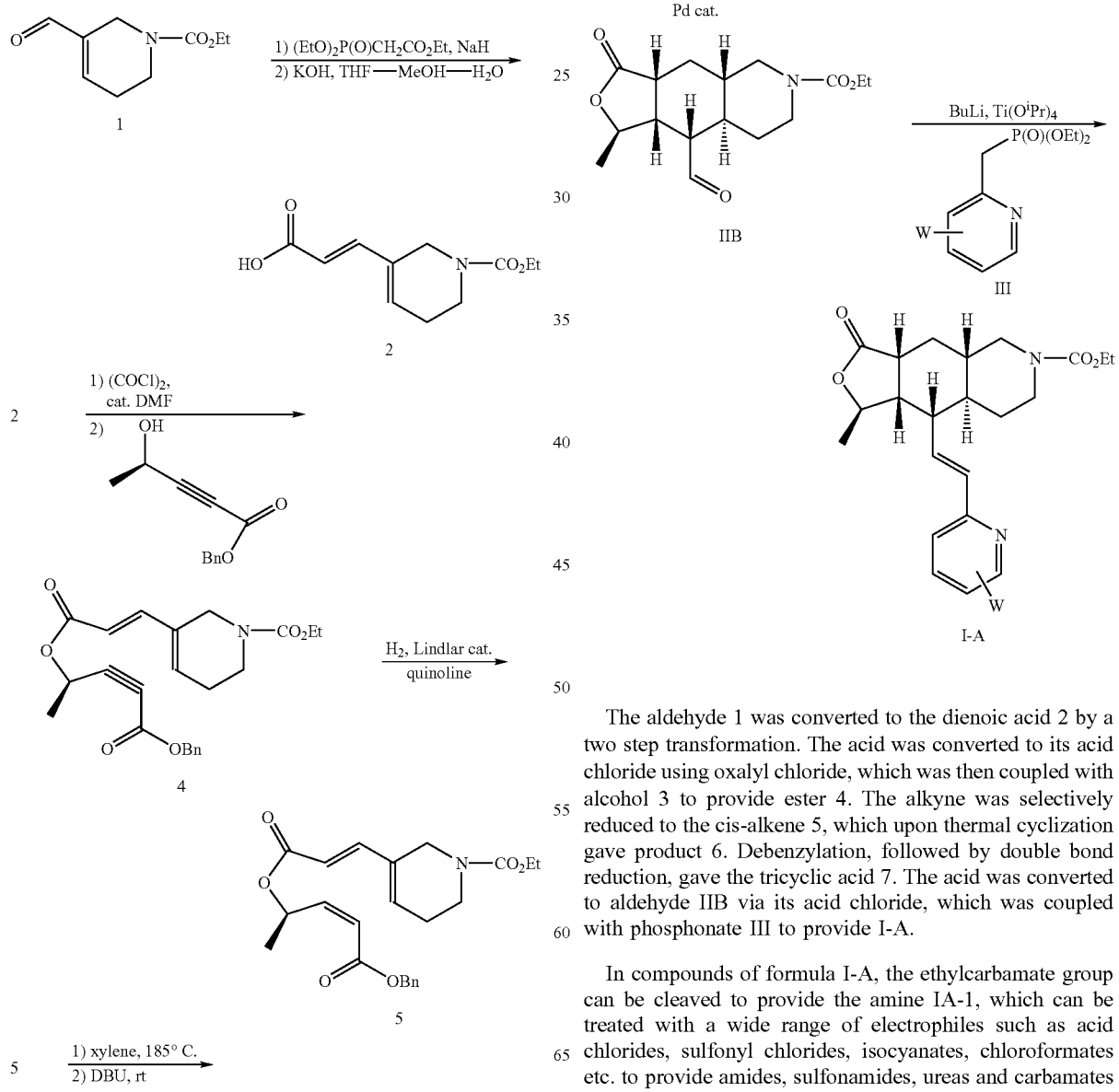

The aldehyde 1 was converted to the dienoic acid 2 by a two step transformation. The acid was converted to its acid chloride using oxalyl chloride, which was then coupled with alcohol 3 to provide ester 4. The alkyne was selectively reduced to the cis-alkene 5, which upon thermal cyclization gave product 6. Debenzylation, followed by double bond reduction, gave the tricyclic acid 7. The acid was converted to aldehyde IIB via its acid chloride, which was coupled with phosphonate III to provide I-A.

In compounds of formula I-A, the ethylcarbamate group can be cleaved to provide the amine IA-1, which can be treated with a wide range of electrophiles such as acid chlorides, sulfonyl chlorides, isocyanates, chloroformates etc. to provide amides, sulfonamides, ureas and carbamates etc. as shown in Scheme 2.

Scheme 2:
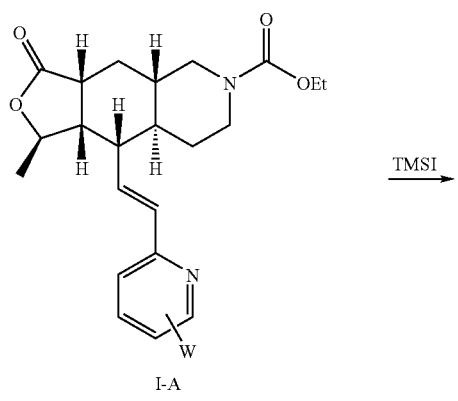
The aldehyde of formula IIB can also be coupled with phosphonate 8 to provide I-A3, which can be transformed into carbamate I-A4 as shown in Scheme 3. Both I-A3 and I-A4 can be converted into diverse analogs using methodologies such as Suzuki coupling, Stille coupling, Buchwald amination etc (Scheme 4).
Scheme 3:
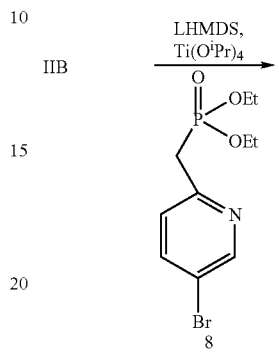
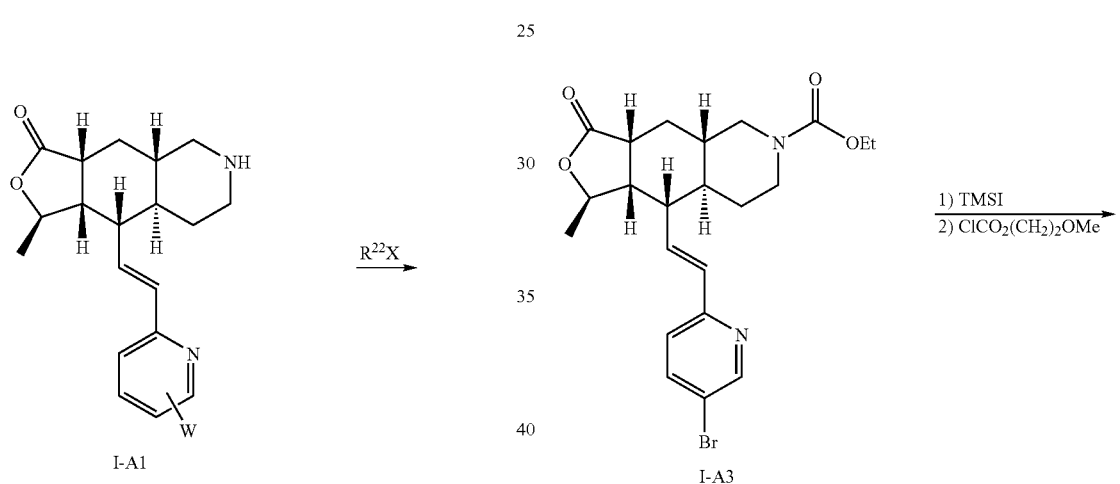
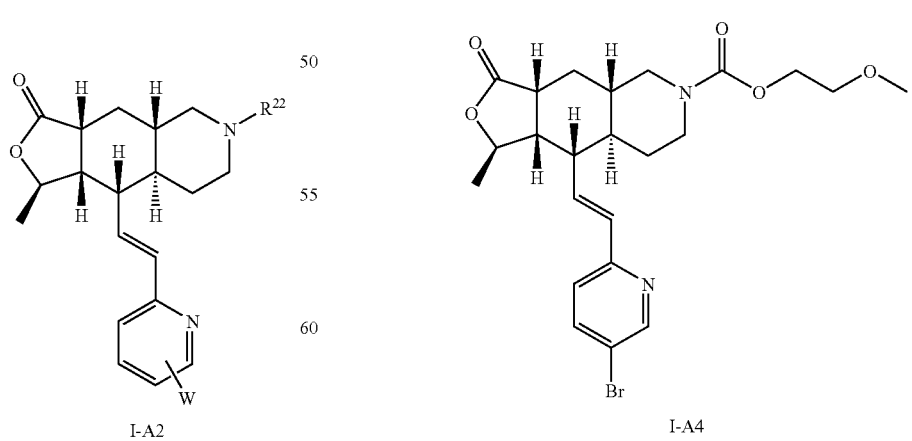

Scheme 4:

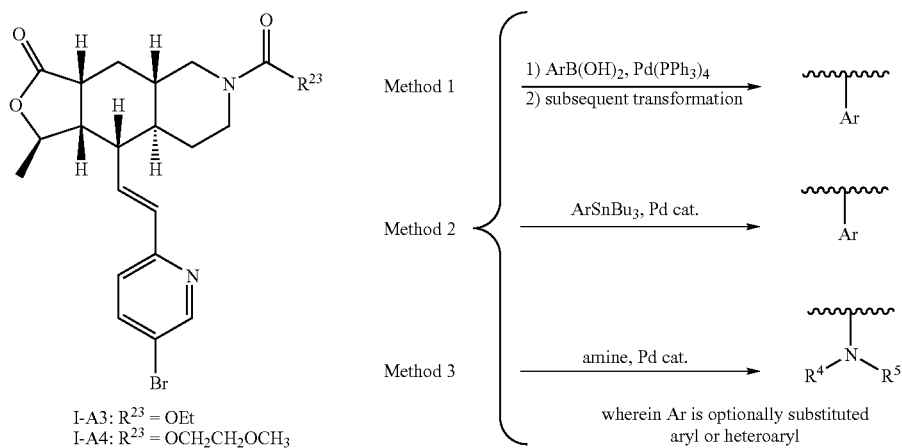

I-A3: R²³ = OEt
I-A4: R²³ = OCH₂CH₂OCH₃

The arylbromide I-A3 can also be converted to aniline I-A5, which can be treated with many readily accessible electrophiles such as acid chlorides, sulfonamides, isocyanates etc. to provide the corresponding derivatives I-A6 as shown in Scheme 5.

Scheme 5:

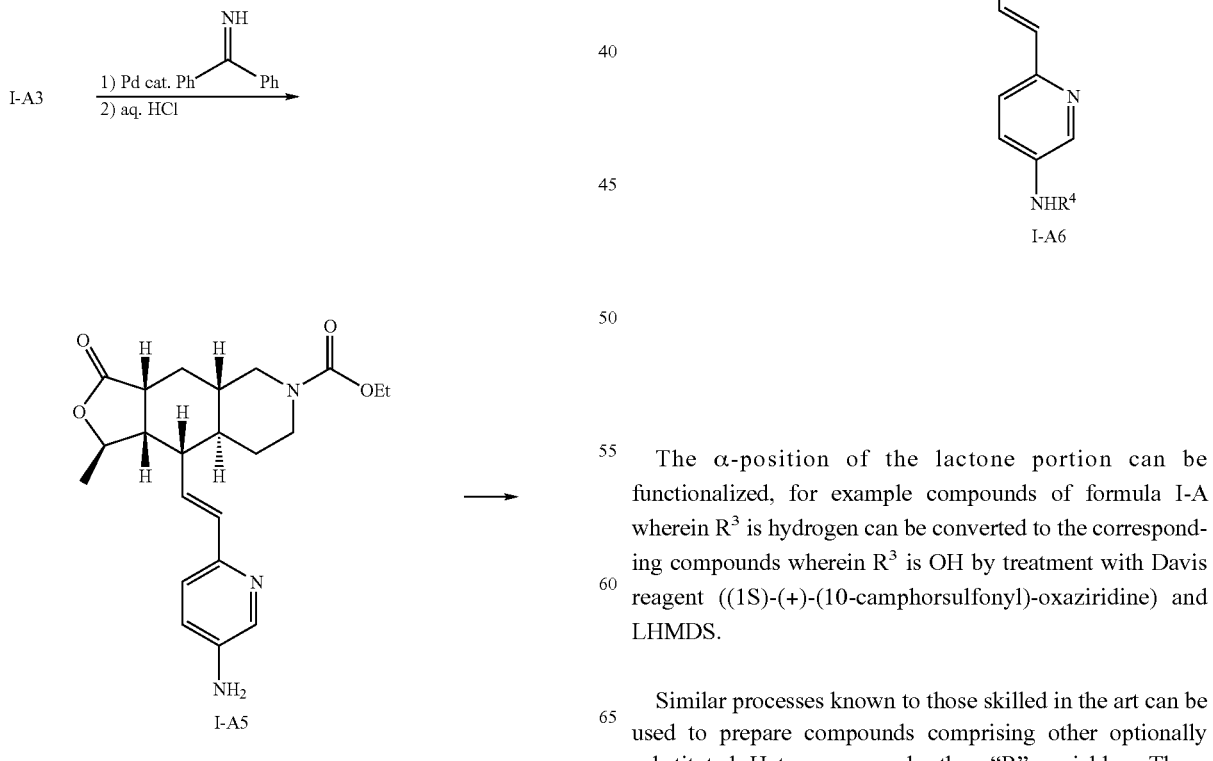

The α-position of the lactone portion can be functionalized, for example compounds of formula I-A wherein $R^3$ is hydrogen can be converted to the corresponding compounds wherein $R^3$ is OH by treatment with Davis reagent ((1S)-(+)-(10-camphorsulfonyl)-oxaziridine) and LHMDS.

Similar processes known to those skilled in the art can be used to prepare compounds comprising other optionally substituted Het groups and other "R" variables. Those skilled in the art will also recognize that the processes are equally applicable to preparing optically active or racemic compounds.

Compounds of formula I wherein $R^9$ is hydrogen can be converted to the corresponding compound wherein $R^9$ is hydroxy by heating with an oxidizing agent such as $SeO_2$.

Phosphonates of formula III wherein W is aryl or $R^{21}$-aryl can be prepared by a process similar to that described immediately below for preparing the trifluoromethyl-phenyl-substituted compound, IIIa.

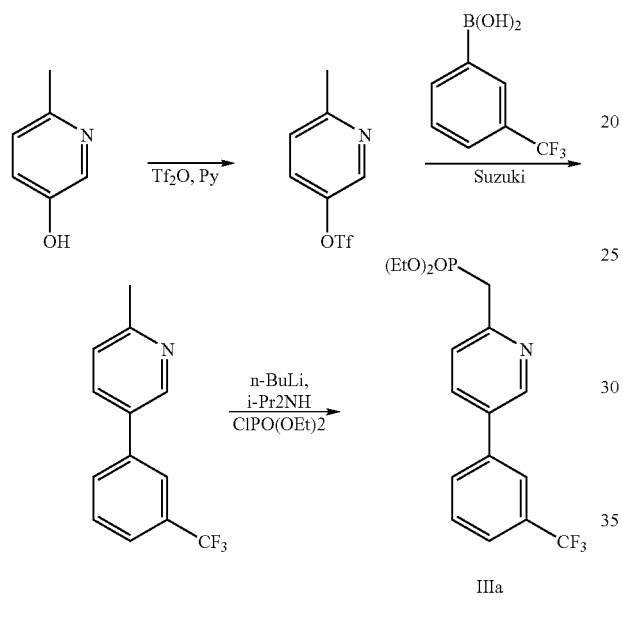

Commercially available hydroxypyridine derivative is converted to the corresponding triflate using triflic anhydride, which is then coupled with commercially available boronic acid in the presence of Pd(0) under Suzuki conditions. The resulting product is converted to the phosphonate by treatment with n-butyllithium followed by quenching with diethylchlorophosphate.

Starting materials for the above processes are either commercially available, known in the art, or prepared by procedures well known in the art.

Reactive groups not involved in the above processes can be protected during the reactions with conventional protecting groups which can be removed by standard procedures after the reaction. The following Table A shows some typical protecting groups:

TABLE A

| Group to be Protected | Group to be Protected and Protecting Group |
|---|---|
| —COOH | —COOalkyl, —COObenzyl, —COOphenyl |

TABLE A-continued

| Group to be Protected | Group to be Protected and Protecting Group |
|---|---|
| \NH/ | \NCOalkyl/, \NCObenzyl/, \NCOphenyl/, \NCH₂OCH₂CH₂Si(CH₃)₃/, \NC(O)OC(CH₃)₃/, \N-benzyl/, \NSi(CH₃)₃/, \NSi(CH₃)₂—C(CH₃)₃/ |
| —NH₂ | 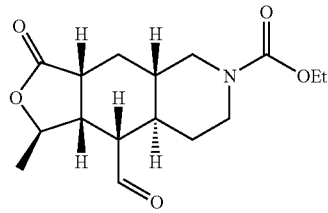 |
| —OH | —OCH₃, —OCH₂OCH₃, —OSi(CH₃)₃, —OSi(CH₃)₂—C(CH₃)₃  or  —OCH₂phenyl |

Following are examples of preparing starting materials and compounds of formula I.

Preparation 1

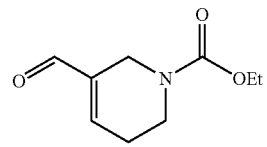

Step 1:

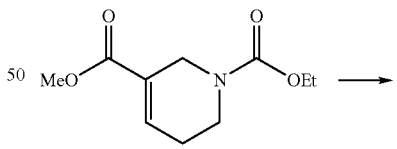

To a solution of 5,6-dihydro-2H-pyridine-1,3-dicarboxylic acid 1-ethyl ester 3-methyl ester (35.4 g, 166 mmol) in $CH_2Cl_2$ (600 ml) at −78° C. was slowly added a solution of 1M DIBAL (365 ml, 365 mmol, 2.2 eq.) in $CH_2Cl_2$, and the mixture stirred for 1.5 hr. The reaction was quenched by the addition of 1 liter of saturated aq. Rochelle's salt and the organic layer was separated. The aqueous layer was extracted with 2×250 ml of $CH_2Cl_2$ and the combined organic layer was washed with 500 ml brine, dried over $MgSO_4$, filtered, concentrated and the resultant crude was chromatographed with 40% EtOAc-hex to provide 17 g (55%) of alcohol as an oil.

To a solution of above alcohol (17.0 g, 92 mmol) in 150 ml of $CH_2Cl_2$ at rt was added $NaHCO_3$ (15.4 g, 183 mmol, 2 eq.) and Dess-Martin reagent (46.7 g, 110 mmol, 1.2 eq.) and the suspension was stirred for 45 min. To this was added 300 ml of $Et_2O$ and a solution of $Na_2S_2O_3 \cdot 5H_2O$ (70 g, 282 mmol, 2 eq.) and $NaHCO_3$ (15.4 g, 183 mmol, 2 eq.) in 600 ml $H_2O$. The mixture was stirred vigorously until the two layers became clear. The organic layer was separated and the aqueous layer was extracted with 2×150 ml of $Et_2O$. The combined organic layer was washed with 300 ml each of aq. $Na_2S_2O_3/NaHCO_3$ and brine, dried over $MgSO_4$, filtered and evaporated to give 15.3 g (91%) of oil. HRMS: 184.0966 ($MH^+$).

Step 2:

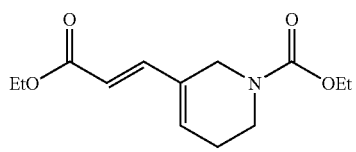

To a suspension of 60% NaH (4.35 g, 109 mmol, 1.3 eq.) in THF (300 ml) at 0° C. was added dropwise triethyl phosphonoacetate (20 ml, 109 mmol, 1.3 eq) and the mixture was stirred at 0° C. for 30 min. To this was added a solution of the product of Step 1 (15.3 g, 83.5 mmol) and the mixture was stirred for 30 min. at 0° C. The reaction was quenched by the addition of 600 ml of aq. $NH_4Cl$, the THF was evaporated and the aqueous slurry was extracted with 3×200 ml of $Et_2O$. The combined organic layer was washed with 200 ml of brine, dried over $MgSO_4$, filtered, concentrated and chromatographed with 15% EtOAc-hex to provide 19.9 g (94%) of oil. MS: 254 ($MH^+$)

Step 3:

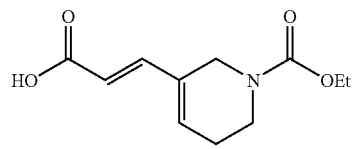

To a solution of the product of Step 2 (19.9 g, 79 mmol) in 100 ml each of $CH_3OH$, THF and $H_2O$ was added KOH (13.3 g, 237 mmol, 3 eq.) and the mixture was stirred at rt for 2 h. The mixture was diluted with 200 ml of $H_2O$, acidified with 1N HCl to ~pH 2 and extracted with 3×200 ml of EtOAc. The combined organic layer was washed with 200 ml each of $H_2O$ and brine, dried over $MgSO_4$, filtered and evaporated to give 17.0 g (96%) of pale-yellow solid. HRMS: 226.1083 ($MH^+$)

Step 4:

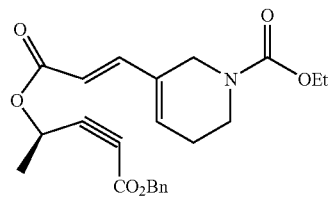

To a solution of dienoic acid (17.0 g, 76 mmol) in 400 ml $CH_2Cl_2$ at rt was added oxalyl chloride (13.2 ml, 151 mmol, 2 eq.) and DMF (120 μl, 1.6 mmol, 2 mol %). The mixture was stirred for 1 h, concentrated and evaporated with 100 ml anhydrous toluene to provide the acid chloride.

To a solution of the above acid chloride in 200 ml $CH_2Cl_2$ at 0° C. was added DMAP (925 mg, 7.6 mmol, 0.1 eq.), a solution of the product of Step 3 (15.4 g, 75 mmol, 1.0 eq.) in 15 ml $CH_2Cl_2$ followed by $Et_3N$ (12.7 ml, 91 mmol, 1.2 eq.). The mixture was stirred for 1.5 hr at 0° C., then diluted with 600 ml of $Et_2O$. The solution was washed successively with 200 ml $H_2O$, 2×200 ml 1N HCl, 200 ml aq. $NaHCO_3$ and 200 ml brine. It was dried over anhydrous $MgSO_4$, filtered, concentrated and chromatographed with 20% EtOAc-hex to provide 20 g (78%) of resin. HRMS: 412.1764 ($MH^+$).

Step 5:

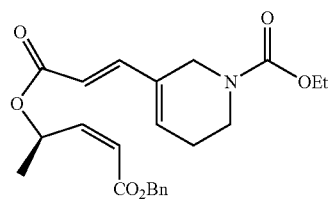

A suspension of the product of Step 4 (10 g, 29 mmol), quinoline (700 μl, 5.9 mmol, 0.2 eq.) and Lindlar catalyst (1.0 g, 10 wt %) in 150 ml THF was stirred under 1 atm. $H_2$ for 2.5 h. Another batch of 10 g of the product of Step 4 was similarly reduced with Lindlar catalyst. The batches were combined, filtered through celite, evaporated and the residue was re-dissolved in 600 ml EtOAc. It was washed with 3×200 ml of 1N HCl and 200 ml of brine, dried over $MgSO_4$, filtered and evaporated to give 20 g of resin which was used immediately for the Diels-Alder reaction in Step 6. HRMS: 414.1919 ($MH^+$).

Step 6:

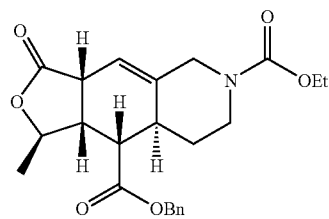

A solution of the product of Step 5 (20.0 g) in 500 ml toluene was heated in a pressure vessel at 185° C. for 6 h. It was cooled to rt, treated with DBU (1.8 ml, 12 mmol, 0.2 eq.) for 1 h, concentrated and chromatographed with 25% EtOAc-hex to provide 11.3 g (56%) of the cyclized exo product. HRMS: 414.1923 ($MH^+$).

Step 7:

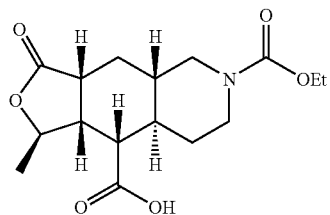

A suspension of the product of Step 6 (11.2 g, 27 mmol), 10% Pd—C (1.2 g, 10 wt %) in 200 ml EtOAc was stirred under 1 atm. $H_2$ until the reaction was complete. It was filtered through celite, concentrated and re-dissolved in 200 ml of $CH_3OH$. To this was added 900 mg of $PtO_2$ and the suspension was shaken under 50 atm. of $H_2$ in a parr vessel. The mixture was filtered through celite and concentrated to provide 8.5 g of resin. HRMS: 326.100 ($MH^+$).

Step 8:

To a solution of the product of Step 7 (415 mg, 1.28 mmol) in 10 ml $CH_2Cl_2$ at rt was added oxalyl chloride (225 μl, 2.58 mmol, 2 eq.) followed by 1 drop of DMF. The solution was stirred at rt for 1 h, at which time there was no evolution of gas. It was concentrated and azeotroped with anhydrous toluene to give the acid chloride. The acid chloride was dissolved in 6 ml of anhydrous toluene, cooled to 0° C. and $Pd(PPh_3)_4$ (74 mg, 0.064 mmol, 5 mol %) was added, followed by $Bu_3SnH$ (520 μl, 1.93 mmol, 1.5 eq.). The mixture was stirred at 0° C. for 3 hr, concentrated and chromatographed with 50% EtOAc-hex to provide 360 mg (91%) of the title compound as a resin. MS: 310.1 ($MH^+$).

Preparation 2

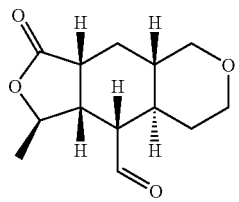

3-Formyl-5,6-dihydro-2H-pyran was converted to the tricyclic aldehyde using similar procedure described above for the corresponding amine analogs.

Preparation 3

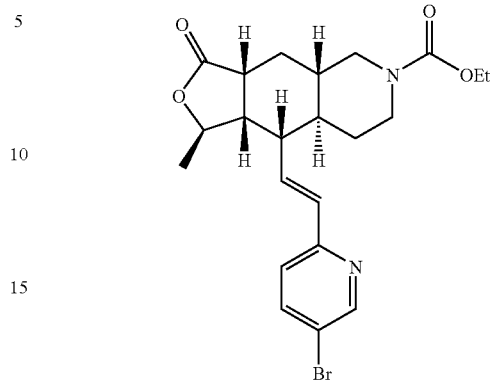

Reaction Scheme:

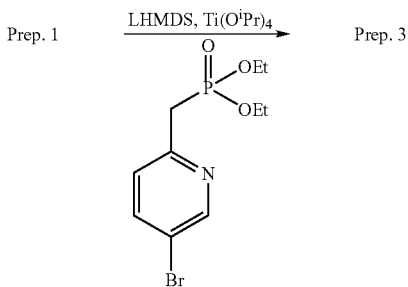

To a solution of the phosphonate (3.49 g, 11.3 mmol, 2 eq.) in THF (50 ml) at 0° C. was added a 1M solution of LHMDS in THF (11.3 ml, 11.3 mmol, 2eq.). After stirring for 10 min., $Ti(O^iPr)_4$ (3.4 ml, 11.3 mmol, 2 eq.) was added, followed by a solution of Preparation 1 (1.75 g, 5.7 mmol, 1 eq.) in THF (10 ml), and the mixture was stirred for 1 h under $N_2$. The reaction mixture was poured into 5% aqueous tartaric acid solution (100 ml) and extracted with EtOAc (3×100 ml). The combined organic layers were washed with brine (150 ml), dried with $MgSO_4$, filtered and evaporated to dryness. Purification by silica gel chromatography eluting with 5% $CH_3OH$—$CH_2Cl_2$ yielded 1.80 g (70%) of the title compound as a pale yellow foam. $^1H$ NMR (400 MHz, $CDCl_3$): 8.59 (d, J=4.8 Hz, 1H), 7.76 (dd, J=3 Hz, 8.4 Hz, 1H), 7.06 (d, J=8.4 Hz, 1H), 6.56 (dd, J=9.6 Hz, 15.2 Hz, 1H), 6.45 (d, J=15.2 Hz, 1H), 4.73 (m, 1H), 4.35–4.05 (m, 2H), 4.12 (q, J=6.8 Hz, 2H), 2.73–2.69 (m, 2H), 2.47–2.35 (m, 3H), 1.96 (q, 6.0 Hz, 1H), 1.74 (d, J=12.8 Hz, 1H), 1.41 (d, J=6.0 Hz, 3H), 1.35–1.18 (m, 7H), 1.10–0.98 (m, 1H).

Preparation 4

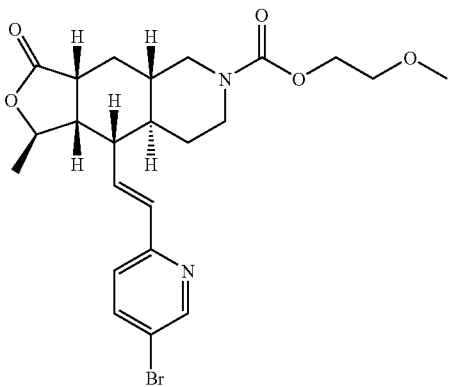

To a solution of Preparation 3 (0.270 g, 0.58 mmol) in CH$_2$Cl$_2$ (15 ml) was added TMSI (624 μl, 4.4 mmol, 7.5 eq.), and the mixture was heated to reflux. After 6 h, the mixture was poured onto aqueous NaHCO$_3$ (30 ml) and extracted with CH$_2$Cl$_2$ (3×15 ml). The combined organic layers were washed with brine, dried with MgSO$_4$, filtered and evaporated to dryness resulting in 209 mg of amine (92%).

To the above product in CH$_2$Cl$_2$ (15 ml) at 0° C. was added Et$_3$N (97 μl, 0.69 mmol, 1.3 eq.) and chloroformic acid 2-methoxyethyl ester (68 l, 5.9 mmol, 1.1 eq.); the mixture was allowed to slowly warm to rt while stirring under N$_2$. After 1 h, the mixture was poured onto water (30 ml) and extracted with CH$_2$Cl$_2$ (3×15 ml). The combined organic layers were washed with brine (30 ml), dried with MgSO$_4$, filtered and evaporated to dryness. Purification by silica gel chromatography, eluting with 3% CH$_3$OH—CH$_2$Cl$_2$, yielded 183 mg of the title compound as a white solid (69%). $^1$H NMR (400 MHz, CDCl$_3$): 8.59 (d, J=2.4 Hz, 1H), 7.76 (dd, J=2.4, 8.2 Hz, 1H), 7.06 (d, J=8.3 Hz, 1H) 6.56 (dd, J=9.6, 15.4 Hz, 1H), 6.45 (d, J=15.4 Hz, 1H), 4.72 (m, 1H), 4.1–4.28 (m, 4H), 3.59 (t, J=4.49 Hz, 2H), 3.38 (s, 3H), 2,75–2.68 (m, 2H), 2.32–2.51 (m, 3H), 1.96 (dd, J=6.3, 12.8 Hz, 1H), 1.73 (d, J=12.5 Hz, 1H), 1.41 (d, J=5.95 Hz, 3H), 1.37–1.00 (m, 4H).

Preparation 5

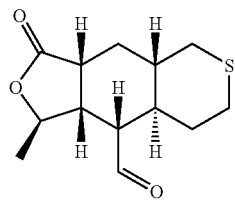

Step 1:

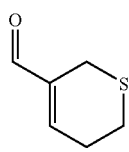

The thiopyran enal was prepared according to the procedure of McGinnis and Robinson, J. Chem. Soc., 404 (1941), 407.

Step 2:

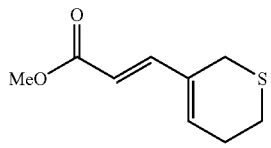

To a suspension of 60% NaH (6.3 g, 158 mmol, 1.3 eq.) in THF (200 ml) at 0° C. was added methyl diethylphosphonoacetate (29 ml, 158 mmol, 1.3 eq.) and the mixture was stirred at 0° C. for 30 min. The solution was then transferred to a solution of the product of Step 1 (15.6 g, 122 mmol) in THF (100 ml) and stirred at 0° C. for 1 h. The reaction was quenched by the addition of aq. NH$_4$Cl (500 ml) and the THF was evaporated. The aqueous phase was extracted with Et$_2$O (3×200 ml) and the combined organic layer was washed with H$_2$O and brine (200 ml each). The solution was dried over MgSO$_4$, concentrated and the resultant residue was chromatographed with 5% EtOAc-hexane to provide 13.0 g (58%) of oil. $^1$H NMR (400 MHz, CDCl$_3$) 7.26 (d, J=15.9 Hz, 1H), 6.26 (t, J=4.4 Hz, 1H), 5.78 (dd, J=15.9, 0.6 Hz, 1H), 3.75 (s, 3H), 3.25–3.23 (m, 2H), 2.71 (t, J=5.8 Hz, 2H), 2.57–2.53 (m, 2H).

Step 3:

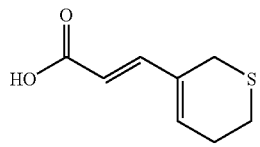

To a solution of the product of Step 2 (13.0 g, 70.6 mmol) in THF and MeOH (50 ml each) was added a solution of KOH (11.9 g, 212 mmol, 3.0 eq.) in H$_2$O (50 ml). The mixture was stirred at rt for 1 h, diluted with H$_2$O (100 ml) and acidified with 1N HCl. The aqueous phase was extracted with EtOAc (3×200 ml) and the combined organic layer was washed with H$_2$O and brine (300 ml each). The solution was dried over MgSO$_4$, filtered and evaporated to give 11.66 g (97%) of pale-yellow solid. $^1$H NMR (400 MHz, CDCl$_3$) 7.34 (d, J=15.6 Hz, 1H), 6.32 (t, J=4.4 Hz, 1H), 5.78 (d, J=15.6 Hz, 1H), 3.26 (d, J=1.6 Hz, 2H), 2.72 (t, J=5.8 Hz, 2H), 2.59–2.55 (m, 2H).

Step 4:

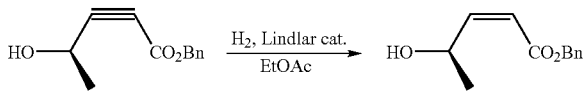

4

To a solution of 4 (5.2 g) in EtOAc (120 ml) was added Lindlar catalyst (520 mg) and the suspension was stirred under 1 atm. H$_2$. Another portion of catalyst (500 mg) was added after 45 min. and the mixture stirred for further 30 min. The mixture was filtered through a celite pad and evaporated to provide 5.2 g (99%) of the desired alkene. $^1$H NMR (400 MHz, CDCl$_3$) 7.38–7.26 (m, 5H), 6.32 (dd, J=11.9, 6.6 Hz, 1H), 5.86 (d, J=12.0 Hz, 1H), 5.18 (s, 2H), 5.12–5.07 (m, 1H), 3.20 (br s, 1H), 1.34 (d, J=6.6 Hz, 3H).

Step 5:

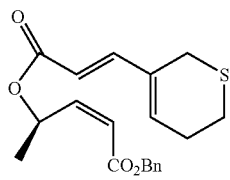

To a solution of the product of Step 3 (2.45 g, 14.39 mmol) in $CH_2Cl_2$ (60 ml) at 0° C. was added DCC (3.27 g, 15.85 mmol, 1.1 eq.) followed by DMAP (352 mg, 2.88 mmol, 0.2 eq.) and the mixture was stirred at 0° C. for 30 min. To this was added a solution of 3.27 g (15.85 mmol, 1.1 eq.) of the alcohol of Step 4 in 10 ml of $CH_2Cl_2$ and the mixture was stirred at 0° C. for 5 hr and at rt for 1 hr. The solution was diluted with 350 ml of $Et_2O$ and washed with 2×200 ml of aq. citric acid, 200 ml of aq. $NaHCO_3$ and 200 ml of brine. The solution was dried over $MgSO_4$, filtered, concentrated and the resultant residue was chromatographed with 6% EtOAc-hex to provide 2.1 g (41%) of resin. $^1$H NMR (400 MHz, $CDCl_3$) 7.38–7.32 (m, 5H), 7.45 (d, J=16.0 Hz, 1H), 6.38–6.34 (m, 1H), 6.26 (t, J=4.6 Hz, 1H), 6.21 (d, J=11.6 Hz, 1H), 6.19 (d, J=11.2 Hz, 1H), 5.85 (dd, J=11.6, 1.2 Hz, 1H), 5.76 (d, J=16.0 Hz, 1H), 5.18 (d, J=1.2 Hz, 2H), 3.24 (d, J=2.0 Hz, 2H), 2.71 (t, 2H, J=5.6 Hz, 2H), 2.56–2.52 (m, 2H), 1.41 (d, J=6.4 Hz, 3H)

Step 6:

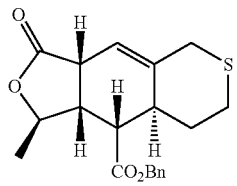

A solution of the product of Step 5 (2.1 g, 5.85 mmol) in m-xylene (50 ml) was heated at 200° C. for 6 h in sealed tube. The solution was cooled to rt and stirred with DBU (178 l, 1.19 mmol, 0.2 eq.) for 1 h, concentrated and chromatographed with 15% EtOAc-hexane to provide 1.44 g (69%) of the desired exo product. $^1$H NMR (400 MHz, $CDCl_3$) 7.39–7.35 (m, 5H), 5.46 (br s, 1H), 5.16 (ABq, J=21.6, 12.0 Hz, 2H), 4.42 (dq, J=9.2, 6.0 Hz, 1H), 3.36–3.33 (m 2H), 3.08 (dd, J=14.4, 2.4 Hz, 1H), 2.85 (ddd, J=13.9, 12.4, 2.5 Hz, 1H), 2.72–2.57 (m, 4H), 2.27-2.21 (m, 1H), 1.47–1.25 (m, 1H), 1.12 (d, J=6.4 Hz, 3H)

Step 7:

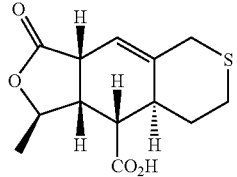

To a solution of the product of Step 6 (750 mg, 2.09 mmol) in $CH_2Cl_2$ (10 ml) at −78° C. was added $BBr_3$ in $CH_2Cl_2$ (4.2 ml of 1M solution). The solution was stirred at −78° C. for 30 min. and at 0° C. for 30 min, then poured into aq. $K_2CO_3$ (100 ml). The aqueous phase washed with $Et_2O$ (2×50 ml) and the organic layer was back extracted with aq. $K_2CO_3$ (50 ml). The combined aqueous phase was acidified with 1N HCl and extracted with EtOAc (3×50 ml). The EtOAc layer was washed with brine (50 ml), dried over $MgSO_4$, filtered and evaporated to provide 500 mg (89%) of acid. $^1$H NMR (400 MHz, $CDCl_3$) 5.50 (br s, 1H), 4.47 (dq, J=9.6, 6.0 Hz, 1H), 3.43–3.39 (m, 1H), 3.36 (d, J=15.6 Hz, 1H), 3.10 (dd, J=14.0, 2.4 Hz, 1H), 2.91–2.84 (m, 1H), 2.82-2.77 (m, 1H), 2.70 (dd, J=10.6, 4.2 Hz, 1H), 2.69–2.63 (m, 1H), 2.57–2.52 (m, 1H), 2.34–2.29 (m, 1H), 1.53–1.42 (m, 1H), 1.34 (d, J=6.0 Hz, 3H).

Step 8:

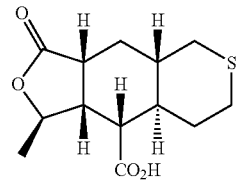

To a solution of the product of Step 7 (500 mg, 1.86 mmol) in MeOH (30 ml) was added AcOH (3 ml) and $PtO_2$ (250 mg) and the suspension was shaken under 40 Psi $H_2$ in a Parr vessel for 1.5 days. The catalyst was filtered off with a celite pad, the solution was concentrated and the resultant residue was dissolved in AcOH—MeOH—$CH_2Cl_2$ mixture (0.5:2:97.5 v/v/v/) and filtered through a short $SiO_2$ column to provide 400 mg (79%) of the reduced product as a resin which solidified on standing. $^1$H NMR (400 MHz, $CDCl_3$) 4.68 (dq, J=9.4, 5.9 Hz, 1H), 2.76–2.69 (m, 2H), 2.60–2.55 (m, 3H), 2.49 (d, J=11.6 Hz, 1H), 2.10 (br s, 1H), 1.93 (ddd, J=13.5, 6.0, 2.7 Hz, 1H), 1.60–1.48 (m, 2H), 1.45–1.19 (m, 3H), 1.33 (d, J=5.6 Hz, 3H).

Step 9:

To a solution of the product of Step 8 (97 mg, 0.36 mmol) in $CH_2Cl_2$ (4 ml) was added oxalyl chloride (94 µl) followed by 1 drop of DMF. The solution was stirred for 1 h at rt and concentrated to provide the crude acid chloride which was dissolved in toluene (3 ml) and cooled to 0° C. $Pd(PPh_3)_4$ (42 mg, 0.04 mmol, 0.1 eq.) was added, followed by $Bu_3SnH$ (94 µl). The mixture was stirred at 0° C. for 3 h, concentrated and chromatographed with 25% EtOAc-hexane to provide 73 mg (80%) of aldehyde as white solid. $^1$H NMR (400 MHz, $CDCl_3$) 9.75 (d, J=2.8 Hz, 1H), 4.62 (dq, J=9.7, 6.0 Hz, 1H), 2.8–2.70 (m, 2H), 2.65–2.55 (m, 3H), 2.50 (d, J=7.2 Hz), 2.10 (ddd, J=13.2, 6.4, 3.0 Hz, 1H), 1.94 (ddd, J=13.6, 6.0, 3.0, 1H), 1.69 (dq, J=10.9 Hz, 3.00 Hz, 1H), 1.58–1.48 (m, 1H), 1.42–1.20 (m, 3H), 1.33(d, J =6.4 Hz, 3H).

Preparation 6

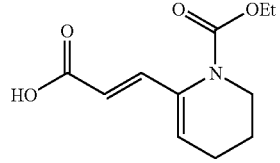

Step 1:

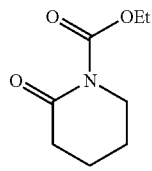

δ-Valerolactam was dissolved in THF (250 ml) and cooled to −78° C. n-BuLi (28.44 ml, 1.1 eq, 2.5 M solution in hexanes) was added dropwise. The mixture was stirred for 30 min, then ethyl chloroformate (6.49 ml, 1.05 eq) was added and the mixture allowed to warm to rt. Water was added and the organic layer extracted with EtOAc. The combined organic layers were dried and concentrated to give 11.57 g of oil. $^1$H NMR (400 MHz, CDCl$_3$) 4.29 (2 H, q, J=7.2 Hz), 3.71 (2 H, br t, J=5.6 Hz), 2.50 (2 H, br t, J=6.8 Hz), 1.83 (4 H, br s), 1.33 (3 H, t, J=7.2 Hz).

Step 2:

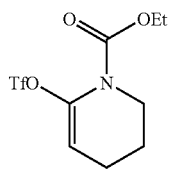

The product of step 1 was dissolved in THF (250 ml) and the solution cooled to −78° C. LHMDS (65 ml, 1 eq, 1 M solution in THF) was added dropwise and the resulting mixture stirred for 30 min. A solution of 2-[N,N-bis(trifluoromethylsulfonyl)-amino]-5-chloropyridine in THF (73 ml) was added dropwise. The resulting mixture was stirred for 10 min and allowed to warm to rt. Water was added and the organic layer extracted with EtOAc. The combined organic layers were dried and concentrated. Chromatography (5–10% EtOAc in Hexane) gave 12.0 g of oil. $^1$H NMR (400 MHz, CDCl$_3$) 5.32 (1 H, t, J=3.6 Hz), 4.24 (2 H, q, J=7.2 Hz), 3.66 (2 H, m), 2.27 (2H, m), 1.78 (2 H, m), 1.30 (3H, J=7.2 Hz).

Step 3:

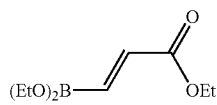

Borane dimethylsulfide complex (5.82 ml, 1.05 eq) was dissolved in THF and cooled to 0° C. (1R)-(+)-α-pinene (22.56 ml, 2.32 eq) was added dropwise, the mixture was stirred at 0° C. for 1 h and at rt for 2 h. The mixture was cooled to −35° C. and ethyl propiolate (6.2 ml, 1 eq) was added dropwise; the mixture was stirred at −35° C. for 45 min and rt for 3 h. Acetaldehyde (48 ml) was added and the mixture heated at 40–41° C. overnight. The volatile organic components were carefully removed under reduced pressure to give 29 g of a mixture of the product and α-pinene (1:2.3 by NMR). $^1$H NMR (400 MHz, CDCl$_3$) characteristic peaks for the product include, 6.95 (1 H, d, J=18.0 Hz), 6.48 (1 H, d, J=18.0 Hz), 4.12 (2 H, q, J=7.2 Hz), 3.60 (4 H, q, J=7.2 Hz).

Step 4:

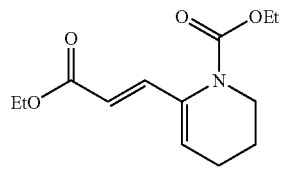

Pd(OAc)$_2$ (592 mg, 10%) and 2-(di-t-butylphosphino)biphenyl (1.57 g, 20%) were dissolved in THF (100 ml). The mixture was stirred for 10 min under N$_2$, then a mixture of the product from step 2 (8 g) and the product from step 3 (20 g, 1.5 eq) in THF (32 ml) were added. KF (4.6 g) was then added and the mixture heated at 55° C. overnight. The mixture was allowed to cool to rt and diluted with EtOAc. The mixture was washed with NaHCO$_3$(sat), NH$_4$Cl(sat), water, and finally dried over MgSO$_4$. Removal of solvents under reduced pressure followed by column chromatography (10% EtOAc in hexane) gave 6 g (89%) of a colorless oil. $^1$H NMR (400 MHz, CDCl$_3$) 7.21 (1 H, d, J=15.6 Hz), 5.88 (1 H, d, J=15.6 Hz), 5.69 (1 H, t, J=4.0 Hz), 4.15 (4 H, m), 3.59 (2 H, m), 2.26 (2H, m), 1.82 (2H, m), 1.25 (6 H, m).

Step 5:

The product from step 4 was dissolved in a 1:1 mixture of MeOH and THF (66 ml). A solution of 1N NaOH (52 ml) was added and the mixture stirred for 2.5 h until no starting material remained.

The mixture was acidified to pH1 with 2 N HCl and extracted with EtOAc. The extracts were washed with NH$_4$Cl (sat), dried, and concentrated under reduced pressure to give 5 g of a solid. $^1$H NMR (400 MHz, CDCl$_3$) 7.30 (1 H, d, J=15.2 Hz), 5.87 (1 H, d, J=15.2 Hz), 5.73 (1 H, m), 4.14 (2H, m), 3.60 (2 H, m), 2.70 (2 H, m), 1.82 (2 H, m), 1.23 (3 H, m).

EXAMPLE 1

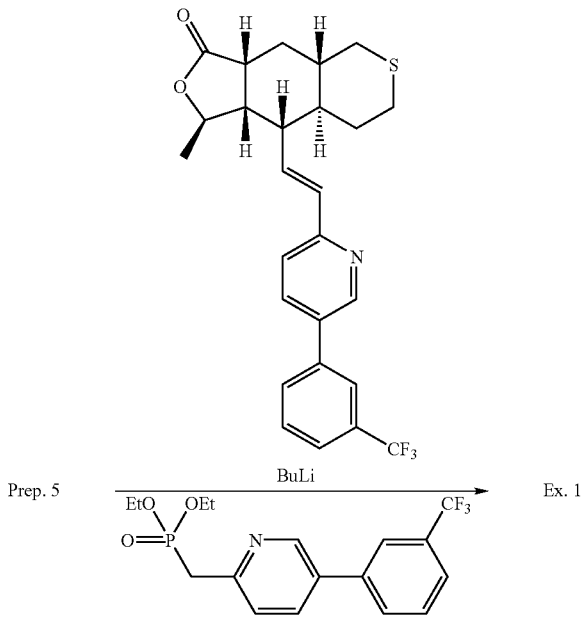

To a solution of phosphonate (156 mg, 0.42 mmol, 2.0 eq.) in THF (1 ml) at 0° C. was added a 2.5 M solution of BuLi in hexanes (170 µl, 0.42 mmol, 2.0 eq.) and the mixture was stirred for 30 min. To this was added a solution of Preparation 5 (53 m, 0.21 mmol) in THF (1.5 ml) and the mixture was stirred at 0° C. for 1 h. The reaction was quenched by the addition of aq. NH$_4$Cl (20 ml), the THF was evaporated and the aqueous phase was extracted with CH$_2$Cl$_2$ (3×10 ml). The combined organic layer was washed with aq. NaHCO$_3$ (15 ml) and brine (15 ml), dried over MgSO$_4$, filtered, concentrated and chromatographed with 40% EtOAc-hex to provide 90 mg (91%) of resin. HRMS: 474.1721.

The thiopyran compound of Example 1 can be converted to the corresponding sulfoxide (1A) and sulfone (1B) by the following procedure:

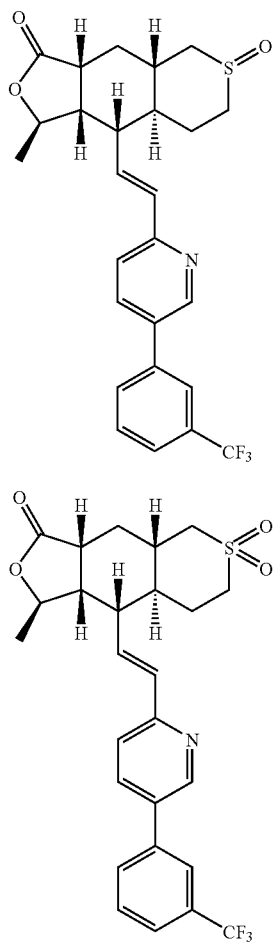

To a solution of Example 1A (70 mg, 0.15 mmol) in AcOH (2 ml) was added CH$_3$SO$_3$H (50 µl, 5 eq.) and NaBO$_3$.4H$_2$O (30 mg, 0.19 mmol, 1.3 eq.), and the mixture was stirred overnight at rt. The acetic acid was evaporated and the resultant residue was taken in aq. NaHCO$_3$—Na$_2$SO$_3$ mixture (25 ml) and extracted with CH$_2$Cl$_2$ (3×15 ml). The combined organic layer was washed with brine (20 ml), dried over MgSO$_4$, filtered, concentrated and purified by preparative thin layer chromatography to provide 11 mg of sulfoxide isomer 1, 4 mg of sulfoxide isomer 2, and 36 mg of sulfone.

Sulfoxide isomer 1: HRMS: 490.1661 (MH+);
Sulfoxide isomer 2: $^1$H NMR (400 MHz, CDCl$_3$): 8.80 (d, J=2.4 Hz, 1H), 7.87 (dd, J=8.0, 2.0 Hz, 1H), 7.81 (s, 1H), 7.76 (d, J=7.6 Hz, 1H), 7.67 (d, J=7.6 Hz, 1H), 7.61 (t, J=7.8 Hz, 1H), 7.27 (d, J=9.6 Hz, 1H), 6.67–6.55 (m, 2H), 4.78–4.71 (m, 1H), 3.44–3.40 (m, 1H), 3.35 (dt, J=12.1, 2.8 Hz, 1H), 2.78–2.71 (m, 1H), 2.64–2.57 (m, 1H), 2.52–2.36 (m, 3H), 2.26–2.21 (m, 1H), 2.04 (ddd, J=13.5, 6.5, 2.7 Hz, 1H), 1.45 (d, J=6.0 Hz, 3H), 1.60–1.25 (m, 6H)

Sulfone: HRMS: 506.1612 (MH$^+$).

EXAMPLE 2

General Procedure:

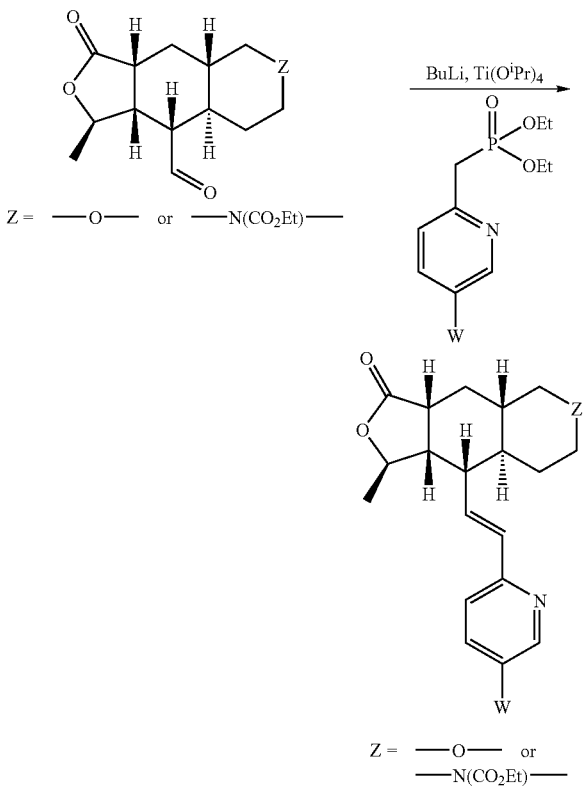

To a solution of phosphonate (2 eq) in THF at 0° C. is added 2.5M BuLi in hexanes (2.0 eq.). After stirring for about 2 h, Ti(O$^i$Pr)$_4$ (2.0 eq) is added, followed by a solution of aldehyde in THF (1.0 eq.). The mixture is stirred at rt for 30 min, diluted with aq. sodium potassium tartrate and extracted with EtOAc. The combined organic layer is washed with brine, dried over MgSO$_4$, filtered, concentrated and purified by column chromatography to provide the product.

Compounds of the following formula were prepared by this general procedure:

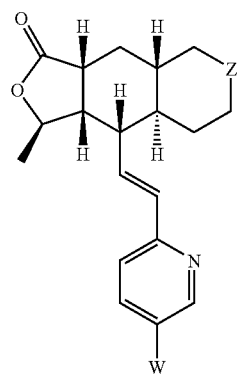

wherein W and Z are as defined in the table:

| Ex. | W | Z | Analytical Data HRMS (MH+) |
|---|---|---|---|
| 2A | 3-CF₃-phenyl | —N(CO₂Et)— | 529.2313 |
| 2B | 3-CF₃-phenyl | —O— | 458.1941 |
| 2C | 3-F-phenyl | —O— | 408.1982 |
| 2D | 3-F-phenyl | —N(CO₂Et)— | 479.2348 |
| 2E | 2-F-phenyl | —N(CO₂Et)— | 479.2339 |
| 2F | 2,3-diF-phenyl | —O— | 426.1881 |
| 2G | 3-Cl-phenyl | —O— | 424.1686 |
| 2H | 2,3-diF-phenyl | —N(CO₂Et)— | 497.2246 |
| 21 | 2-Cl-phenyl | —O— | 424.1684 |
| 2J | 2,3-diCl-phenyl | —O— | 458.1299 |

EXAMPLE 3

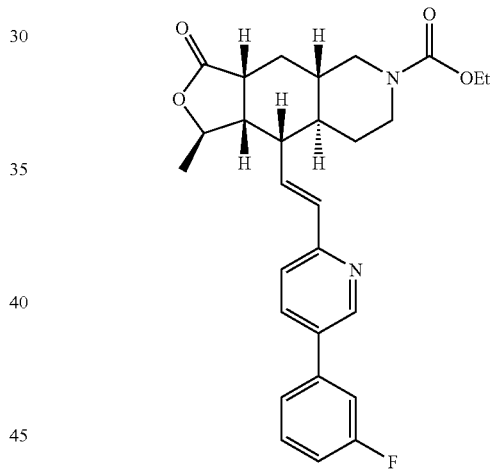

To a solution of Example 2D (380 mg, 0.79 mmol) in THF (7 ml) at −78° C. was added 1M solution of LHMDS in THF (0.95 ml, 0.95 mmol, 1.2 eq.); the mixture was stirred for 30 min at −78° C., 30 min at 0° C., then cooled back to −78° C. To this was added a solution of (1S)-(+)-(10-camphorsulfonyl)oxaziridine (275 mg, 1.1 mmol, 1.5 eq.) in THF (2 ml). The solution was stirred overnight while allowing to warm up to rt. It was diluted with aq. NH₄Cl (100 ml), the THF was evaporated and the aqueous phase extracted with EtOAc (3×30 ml). The combined organic layer was washed with brine (30 ml), dried over MgSO₄, filtered, concentrated and chromatographed with 2% CH₃OH—CH₂Cl₂ to provide 94 mg of resin. HRMS: 495.2291 (MH⁺)

EXAMPLE 4

General Procedure:

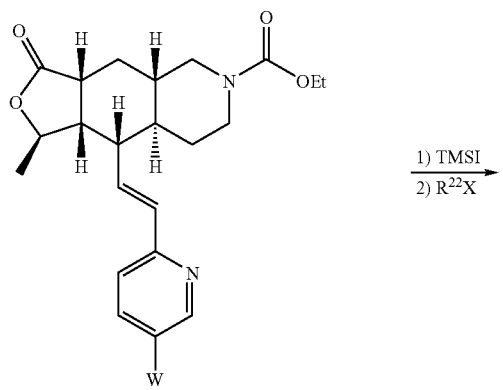

A solution of carbamate and trimethylsilyl iodide (5 eq.) was refluxed for about 5 hr then diluted with aq. NaHCO₃. The aqueous layer was extrated with CH$_2$Cl$_2$ and the combined organic layers was washed with brine, dried over MgSO$_4$, filtered and concentrated to give the amine.

A solution of the amine from above in CH$_2$Cl$_2$ was treated with Et$_3$N (5 eq.) and acid chloride (3 eq) and the reaction was followed by thin layer chromatography. After the reaction was completed, it was subjected to standard aqueous work-up and the crude product was purified by preparative thin layer chromatography or column chromatography to afford the amide.

The amine can similarly be treated with many electrophiles such as sulfonylchlorides, isocyanates, chloroformates and aldehydes etc. to provide the appropriate derivatives. Compounds of the following formula were prepared by this route:

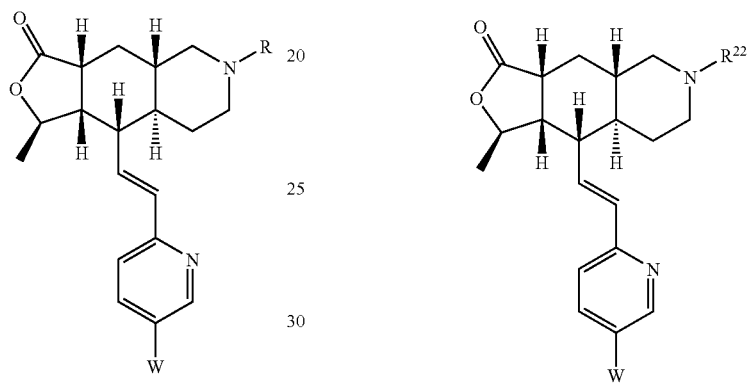

wherein W and $R^{22}$ are as defined in the table:

| Ex. | W | $R^{22}$ | Analytical Data HRMS(MH⁺) |
|---|---|---|---|
| 4A | 3-(CF₃)phenyl | C(O)CH₃ | 499.2209 |
| 4B | 3-(CF₃)phenyl | C(O)cyclopropyl | 525.2372 |
| 4C | 3-(CF₃)phenyl | S(O)₂CH₃ | 535.1873 |

-continued

| Ex. | W | R²² | Analytical Data HRMS(MH⁺) |
|---|---|---|---|
| 4D | 3-CF₃-phenyl | -S(O)₂-ethyl | 549.2031 |
| 4E | 3-CF₃-phenyl | -S(O)₂-isopropyl | 563.2191 |
| 4F | 3-CF₃-phenyl | -C(O)NH-ethyl | 528.2470 |
| 4G | 3-CF₃-phenyl | -C(O)NH-isopropyl | 542.2631 |
| 4H | 3-CF₃-phenyl | -C(O)NH-propyl | 542.2610 |
| 4I | 3-CF₃-phenyl | -C(O)NH-tert-butyl | 556.2786 |
| 4J | 3-CF₃-phenyl | -C(O)O-tert-butyl | 557.2625 |
| 4K | 3-CF₃-phenyl | H | 457.2093 |
| 4L | 3-CF₃-phenyl | -C(O)-ethyl | 513.2347 |

-continued
| Ex. | W | R$^{22}$ | Analytical Data HRMS(MH$^+$) |
|---|---|---|---|
| 4M | 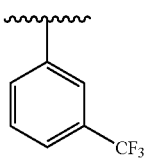 | 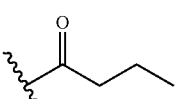 | 527.2523 |
| 4N | 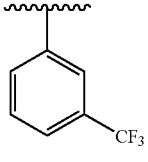 | 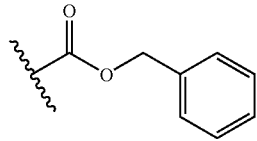 | 591.2464 |
| 4O | 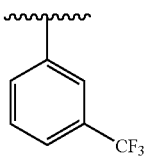 | 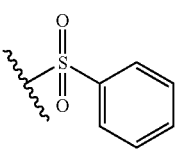 | 591.2021 |
| 4P | 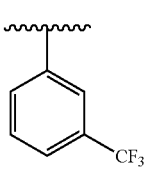 | 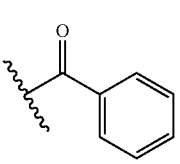 | 561.2375 |
| 4Q | 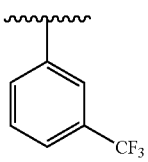 | 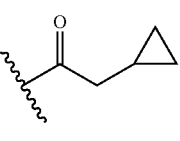 | 539.2530 |
| 4R | 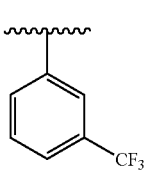 | 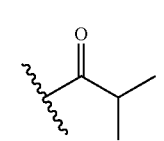 | 527.2517 |
| 4S | 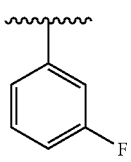 | 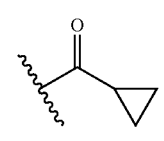 | 475.2406 |
| 4T | 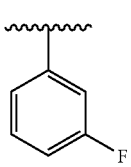 | 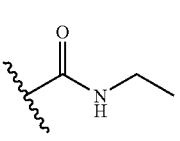 | 478.2515 |
| 4U | 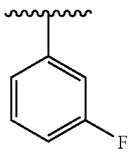 | 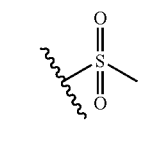 | 485.1901 |

-continued
| Ex. | W | R²² | Analytical Data HRMS(MH⁺) |
|---|---|---|---|
| 4V | 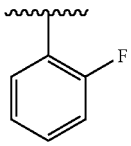 | 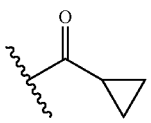 | 475.2411 |
| 4W | 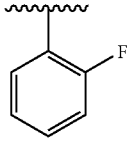 | 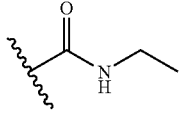 | 478.2520 |
| 4X | 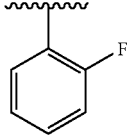 | 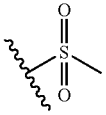 | 485.1906 |
| 4Y | 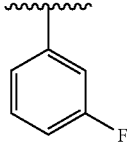 | 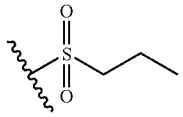 | 513.2227 |
| 4Z | 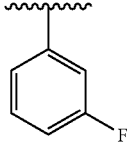 | 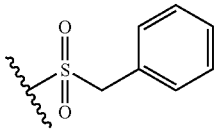 | 561.2214 |
| 4AA | 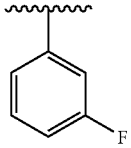 | 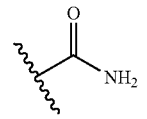 | 450.2187 |
| 4AB | 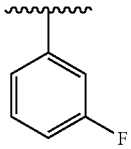 | 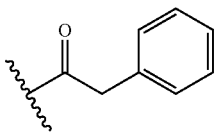 | 525.2554 |
| 4AC | 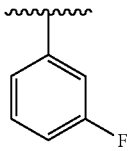 | 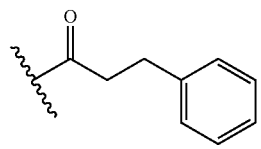 | 539.2716 |
| 4AD | 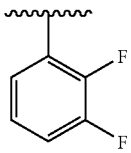 | 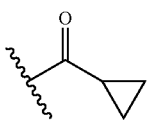 | 493.2297 |

| Ex. | W | $R^{22}$ | Analytical Data HRMS(MH+) |
|---|---|---|---|
| 4AE | 2,3-difluorophenyl | -C(O)NHEt | 496.2403 |
| 4AF | 2,3-difluorophenyl | -S(O)₂Me | 503.1819 |
| 4AG | 3-(trifluoromethyl)phenyl | Me | 471.2255 |

EXAMPLE 5

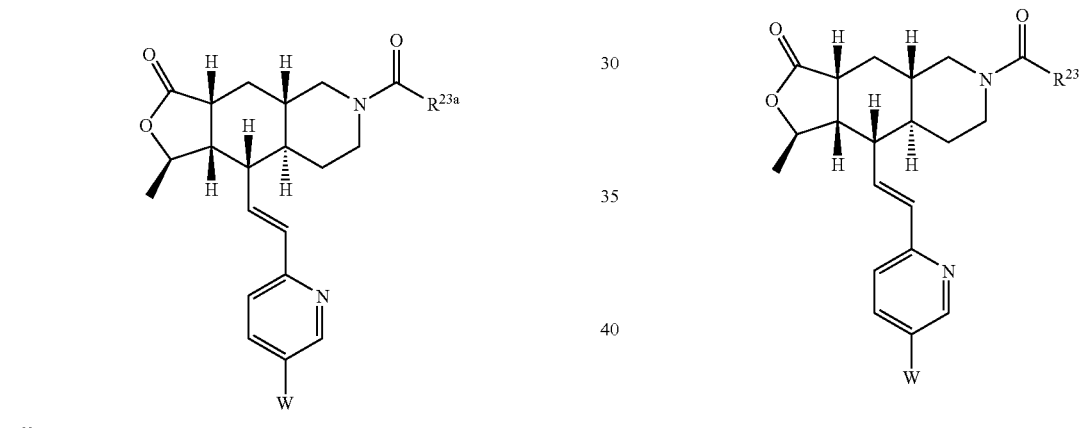

$R^{23a}$ = OEt, OCH₂CH₂OMe

General Procedure:

A solution of a product of Preparation 3 or 4 and W—B(OH)₂, wherein W is optionally substituted phenyl or heteroaryl, $K_2CO_3$ (4 eq.) and Pd(PPh₃)₄ (5 to 10 mol %) in PhMe—EtOH—H₂O (4:2:1 v/v/v) was heated at 100° C. until the reaction was complete. The reaction mixture was diluted with H₂O, extracted with EtOAc, the organic layer was washed with brine, dried over MgSO₄, filtered, concentrated and purified by chromatography to provide the desired compounds. The compounds can be further derivatized.

Using this method, compounds of the following formula were prepared wherein $R^{23}$ and W are as defined in the table:

| Ex. | W | $R^{23}$ | Analytical Data HRMS(MH+) |
|---|---|---|---|
| 5A | 3-cyanophenyl | OEt | 486.2399 |
| 5B | 3-thienyl | OEt | 467.1998 |

-continued

| Ex. | W | R²³ | Analytical Data HRMS(MH⁺) |
|---|---|---|---|
| 5C | 3-(C(Me)=NOH)-phenyl | OEt | 518.2655 |
| 5D | 3-(C(Me)=NOEt)-phenyl | OEt | 546.2964 |
| 5E | 3-furyl | OEt | 451.2239 |
| 5F | 2-pyridyl | OEt | 462.2390 |
| 5G | phenyl | OEt | 461.2438 |
| 5H | 2-Me-phenyl | OEt | 475.2604 |
| 5I | phenyl | OCH₂CH₂OMe | 491.2542 |
| 5J | 3-F-phenyl | OCH₂CH₂OMe | 509.2448 |

EXAMPLE 6

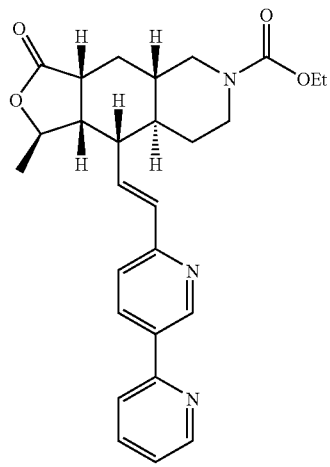

To a solution of Preparation 3 (100 mg, 0.22 mmol) in toluene (5 ml) was added Pd(OAc)₂ (5 mg, 0.022 mmol, 0.1 eq.), (S)-(−)-2,2'-bis(diphenylphoshphino)-1,1'-binaphthyl (13 mg, 0.022 mmol, 0.1 eq.) and 2-tributylstannyl pyridine (119 mg, 0.32 mmol, 1.5 eq.). The mixture was bubbled with N₂ for 5 min., then heated to 100° C. in a pressure tube. After 16 h, the mixture was poured onto aqueous NH₄Cl (15 ml), and extracted with EtOAc (3×15 ml). The combined organic layers were washed with brine, dried with MgSO₄, filtered and evaporated to dryness. Purification by silica gel chromatography, eluting with 2% CH₃OH—CH₂Cl₂, followed by silica gel chromatography eluting with 60% EtOAc-hex, yielded 30 mg (30%) of product. HRMS: 462.2401 (MH⁺)

Using a similar procedure, the following compound 6A was prepared:

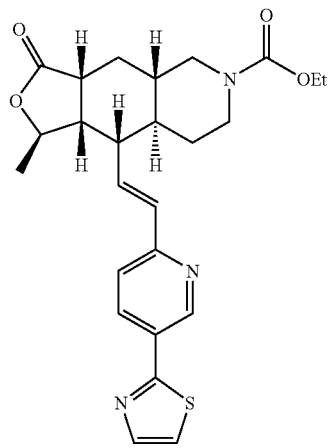

EXAMPLE 6A

MS: 468 (MH+)

EXAMPLE 7

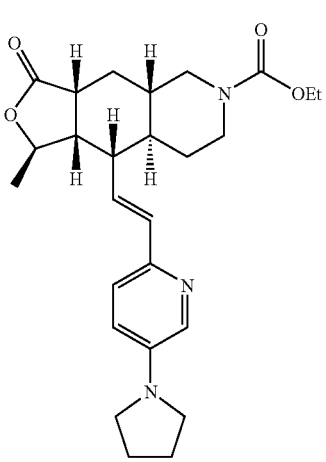

To a solution of Preparation 3 (100 mg, 0.22 mmol) in dry toluene (5 ml) was added pyrrolidine (36 µl, 0.43 mmol, 2 eq.), potassium phosphate (137 mg, 0.65 mmol, 5 eq.), Pd(OAc)$_2$ (3 mg, 0.014 mmol, 0.065 eq.), and 2-(dicyclohexylphosphino)biphenyl (10 mg, 0.028 mmol, 0.13 eq.). The mixture was bubbled with N$_2$ for 5 min., then heated to 100° C. in a pressure tube. After 16 h, the mixture was poured onto water (15 ml) and extracted with EtOAc (3×15 ml). The combined organic layers were washed with brine (15 ml), dried with MgSO$_4$, filtered and evaporated to dryness. Purification by preparative thin layer chromatography, eluting with 5% CH$_3$OH—CH$_2$Cl$_2$, yielded 10 mg of solid HRMS: 454.2696 (MH+)

Using a similar procedure, the following compound was prepared:

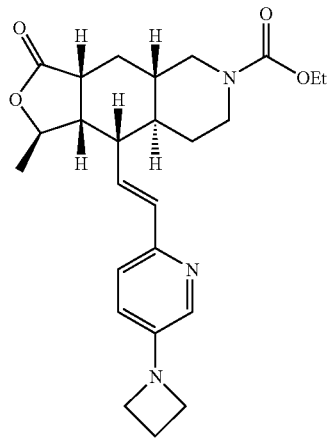

EXAMPLE 7A

HRMS: 440.2558 (MH+)

EXAMPLE 8

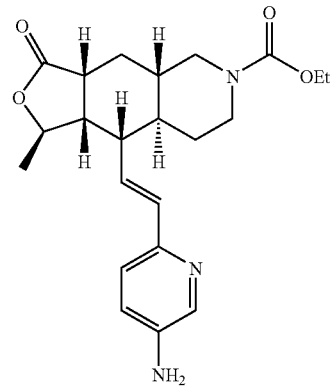

To a solution of Preparation 3 (1.0 g, 2.18 mmol) in ethylene glycol dimethyl ether (25 ml) was added benzophenone imine (550 µl, 3.27 mmol, 1.5eq.), potassium phosphate (1.51 g, 6.6 mmol, 3 eq.), tris(dibenzylideneacetone)dipalladium(0) (200 mg, 0.22 mmol, 0.1 eq.) and 2-(dicyclohexylphosphino)biphenyl (153 mg, 0.44 mmol, 0.2 eq.). The mixture was bubbled with N$_2$ for 5 min., then heated to 100° C. in a pressure tube for 4 h. The mixture was then filtered through celite and evaporated to dryness. To this residue in CH$_2$Cl$_2$ (25 ml) was added concentrated aqueous HCl (545 µL, 6.6 mmol, 3 eq.) and the mixture was stirred at rt. After 16 h, the mixture was diluted with CH$_2$Cl$_2$ (25 ml), poured onto aqueous 1N NaOH (50 ml) and extracted with CH$_2$Cl$_2$ (3×50 ml). The combined organic layers were washed with brine, dried with MgSO$_4$, filtered and evaporated to dryness. Purification by silica gel chromatography, eluting with 2% CH$_3$OH—CH$_2$Cl$_2$ yielded 550 mg (63%) of the title compound. MS: 400 (MH+)

The compound of Example 8 was treated with electrophiles such as acid chlorides, sulfonyl chlorides, isocyanates etc. to provide the following compounds.

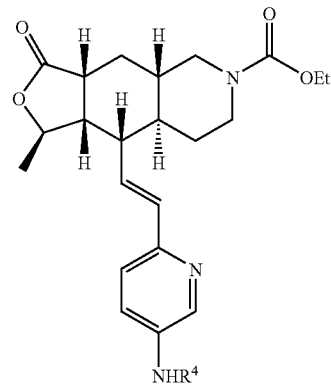

wherein —NHC(O)R²⁶ is as defined in the table:

| Ex. | —NHR⁴ | Analytical Data HRMS(MH⁺) |
|---|---|---|
| 8A | cyclopropyl-C(O)NH– | 468.2505 |
| 8B | 2-thienyl-C(O)NH– | 510.2058 |
| 8C | PhCH₂C(O)NH– | 518.2621 |
| 8D | 2-thienyl-CH₂C(O)NH– | 524.2209 |
| 8E | PhC(O)NH– | 504.2498 |
| 8F | CH₃SO₂NH– | 478.2019 |
| 8G | CH₃CH₂SO₂NH– | 492.2160 |
| 8H | CH₃CH₂NHC(O)NH– | 471.2600 |
| 8I | (CH₃)₂CHSO₂NH– | 506.2318 |

EXAMPLE 9

Using the product of Preparation 6 and the general procedures of Preparation 1, Preparation 3 and Example 5, compounds of the following structure were prepared

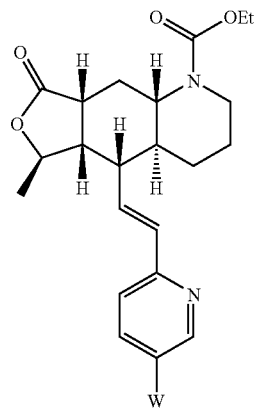

wherein W is as defined in the following table:

| Ex | W | Analytical Data HRMS(MH⁺) |
|---|---|---|
| 9A | 2-fluorophenyl | 479.2350 |
| 9B | 3-fluorophenyl | 479.2350 |
| 9O | 3-cyanophenyl | 486.2399 |

The present invention also relates to a pharmaceutical composition comprising at least one compound of formula I of this invention and a pharmaceutically acceptable carrier. Preferably, one or two compounds of formula I are present in the composition, more preferably one compound of formula I. The compounds of formula I can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily dose of a compound of formulaI for treatment of a disease or condition cited above is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2–4 divided doses. The exact dose, however, is determined by the attending clinician and is dependent on the potency of the compound administered, the age, weight, condition and response of the patient.

The following formulations exemplify some of the dosage forms of this invention. In each, the term "active compound" designates a compound of formula I.

Example A-Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

Example B-Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

The activity of the compounds of formula I can be determined by the following procedures.

In Vitro Testing Procedure for Thrombin Receptor Antagonists:

Preparation of [$^3$H]haTRAP

A(pF-F)R(ChA)(hR)(I$_2$—Y)—NH$_2$ (1.03 mg) and 10% Pd/C (5.07 mg) were suspended in DMF (250 µl) and diisopropylethylamine (10 µl). The vessel was attached to the tritium line, frozen in liquid nitrogen and evacuated. Tritium gas (342 mCi) was then added to the flask, which was stirred at room temperature for 2 hours. At the completion of the reaction, the excess tritium was removed and the reacted peptide solution was diluted with DMF (0.5 ml) and filtered to remove the catalyst. The collected DMF solution of the crude peptide was diluted with water and freeze dried to remove the labile tritium. The solid peptide was redissolved in water and the freeze drying process repeated. The tritiated peptide ([$^3$H]haTRAP) was dissolved in 0.5 ml of 0.1% aqueous TFA and purified by HPLC using the following conditions: column, Vydac C18, 25 cm×9.4 mm I.D.; mobile phase, (A) 0.1% TFA in water, (B) 0.1% TFA in CH$_3$CN; gradient, (A/B) from 100/0 to 40/60 over 30 min; flow rate, 5 ml/min; detection, UV at 215 nm. The radiochemical purity of [$^3$H]haTRAP was 99% as analyzed by HPLC. A batch of 14.9 mCi at a specific activity of 18.4 Ci/mmol was obtained.

Preparation of Platelet Membranes

Platelet membranes were prepared using a modification of the method of Natarajan et al (Natarajan et al, *Int. J. Peptide Protein Res.* 45:145–151 (1995)) from 20 units of platelet concentrates obtained from the North Jersey Blood Center (East Orange, N.J.) within 48 hours of collection. All steps were carried out at 4° C. under approved biohazard safety conditions. Platelets were centrifuged at 100×g for 20 minutes at 4° C. to remove red cells. The supernatants were decanted and centrifuged at 3000×g for 15 minutes to pellet platelets. Platelets were resuspended in 10 mM Tris-HCl, pH 7.5, 150 mM NaCl, 5 mM EDTA, to a total volume of 200 ml and centrifuged at 4400×g for 10 minutes. This step was repeated two additional times. Platelets were resuspended in 5 mM Tris-HCl, pH 7.5, 5 mM EDTA to a final volume of approximately 30 ml and were homogenized with 20 strokes in a Dounce homogenizer. Membranes were pelleted at 41,000×g, resuspended in 40–50 ml 20 mM Tris-HCl, pH 7.5, 1 mM EDTA, 0.1 mM dithiothreitol, and 10 ml aliquots were frozen in liquid N$_2$ and stored at −80° C. To complete membrane preparation, aliquots were thawed, pooled, and homogenized with 5 strokes of a Dounce homogenizer. Membranes were pelleted and washed 3 times in 10 mM triethanolamine-HCl, pH 7.4, 5 mM EDTA, and resuspended in 20–25 ml 50 mM Tris-HCl, pH 7.5, 10 mM MgCl$_2$, 1 mM EGTA, and 1% DMSO. Aliquots of membranes were frozen in liquid N$_2$ and stored at −80° C. Membranes were stable for at least 3 months. 20 units of platelet concentrates typically yielded 250 mg of membrane protein. Protein concentration was determined by a Lowry assay (Lowry et al, *J. Biol. Chem.*, 193:265–275 (1951)).

*High Throughput Thrombin Receptor Radioligand Binding Assay*

Thrombin receptor antagonists were screened using a modification of the thrombin receptor radioligand binding assay of Ahn et al. (Ahn et al, *Mol. Pharmacol.*, 51:350–356 (1997)). The assay was performed in 96 well Nunc plates (Cat. No. 269620) at a final assay volume of 200 µl. Platelet membranes and [$^3$H]haTRAP were diluted to 0.4 mg/ml and 22.2 nM, respectively, in binding buffer (50 mM Tris-HCl, pH 7.5, 10 mM MgCl$_2$, 1 mM EGTA, 0.1% BSA). Stock solutions (10 mM in 100% DMSO) of test compounds were further diluted in 100% DMSO. Unless otherwise indicated, 10 µl of diluted compound solutions and 90 µl of radioligand (a final concentration of 10 nM in 5% DMSO) were added to each well, and the reaction was started by the addition of 100 µl of membranes (40 µg protein/well). The binding was not significantly inhibited by 5% DMSO. Compounds were tested at three concentrations (0.1, 1 and 10 µM). The plates were covered and vortex-mixed gently on a Lab-Line Titer Plate Shaker for 1 hour at room temperature. Packard UniFilter GF/C filter plates were soaked for at least 1 hour in 0.1% polyethyleneimine. The incubated membranes were harvested using a Packard FilterMate Universal Harvester and were rapidly washed four times with 300 µl ice cold 50 mM Tris-HCl, pH 7.5, 10 mM MgCl$_2$, 1 mM EGTA. MicroScint 20 scintillation cocktail (25 µl) was added to each well, and the plates were counted in a Packard Top-Count Microplate Scintillation Counter. The specific binding was defined as the total binding minus the nonspecific binding observed in the presence of excess (50 µM) unlabeled haTRAP. The % inhibition by a compound of [$^3$H]haTRAP binding to thrombin receptors was calculated from the following relationship:

% Inhibition=Total binding-Binding in the presence of a test compound×100 Total binding-Nonspecific binding Materials A(pF-F)R(ChA)(hR)Y—NH$_2$ and A(pF-F)R(ChA)(hR)(I$_2$—Y)—NH$_2$, were custom synthesized by AnaSpec Inc. (San Jose, Calif.). The purity of these peptides was >95%. Tritium gas (97%) was purchased from EG&G Mound, Miamisburg Ohio. The gas was subsequently loaded and stored on an IN/US Systems Inc. Trisorber. MicroScint 20 scintillation cocktail was obtained from Packard Instrument Co.

Protocol for Ex-Vivo Platelet Aggregation in Cynomolgus Whole Blood Drug Administration and Blood Collection:

Conscious chaired cynomolgus monkeys are allowed to equilibrate for 30 min. A needle catheter is inserted into a brachial vein for infusion of test drugs. Another needle catheter is inserted into the other brachial or saphenous vein and used for blood sampling. In those experiments where the compound is administered orally only one catheter is used. A baseline blood sample (1–2 ml) is collected in vacutainer tubes containing a thrombin inhibitor CVS 2139 (100 μg/0.1 ml saline) as an anticoaculant. The drug is then infused intravenously over a period of 30 min. Blood samples (1 ml) are collected at 5, 10, 20, 30 min during and 30, 60, 90 min after termination of the drug infusion. In PO experiments the animals are dosed with the drug using a gavage cannula. Blood samples are collected at 0, 30, 60, 90, 120, 180, 240, 300, 360 min after dosing. 0.5 ml of the blood is used for whole blood aggregation and the other 0.5 ml is used for determining the plasma concentration of the drug or its metabolites. Aggregation is performed immediately after collection of the blood sample as described below.

Whole Blood Aggregation:

A 0.5 ml blood sample is added to 0.5 ml of saline and warmed to 37° C. in a Chronolog whole blood aggregometer. Simultaneously, the impedance electrode is warmed in saline to 37° C. The blood sample with a stir bar is place in the heating block well, the impedance electrode is placed in the blood sample and the collection software is started. The software is allowed to run until the baseline is stabilized and then a 20Ω calibration check is performed. 20Ω is equal to 4 blocks on the graphic produced by the computer software. The agonist (haTRAP) is added by an adjustable volume pipette (5–25 μl) and the aggregation curve is recorded for 10 minutes. Maximum aggregation in 6 minutes following agonist is the value recorded.

In vitro Platelet Aggregation Procedure:

Platelet aggregation studies were performed according to the method of Bednar et al. (Bednar, B., Condra, C., Gould, R. J., and Connolly, T. M., *Throm. Res.*, 77:453–463 (1995)). Blood was obtained from healthy human subjects who were aspirin free for at least 7 days by venipuncture using ACD as anticoagulant. Platelet rich plasma was prepared by centrifugation at 100×g for 15 minutes at 15 deg C. Platelets were pelleted at 3000×g and washed twice in buffered saline containing 1 mM EGTA and 20 μg/ml apyrase to inhibit aggregation. Aggregation was performed at room temperature in buffered saline supplemented with 0.2 mg/ml human fibrinogen. Test compound and platelets were preincubated in 96-well flat-bottom plates for 60 minutes. Aggregation was initiated by adding 0.3 μM haTRAP or 0.1 U/ml thrombin and rapidly vortexing the mixture using a Lab Line Titer Plate Shaker (speed 7). Percent aggregation was monitored as increasing light transmittance at 405 nm in a Spectromax Plate Reader.

In vivo Antitumor Procedure:

Tests in the human breast carcinoma model in nude mouse are conducted according to the procedure reported in S. Even-Ram et. al., *Nature Medicine*, 4, 8 (1988), p. 909–914.

Using the test procedures described above, in the in vitro thrombin receptor antagonist assay, compounds of the invention were found to have IC$_{50}$ values (i.e., the concentration at which a 50% inhibition of thrombin receptor was observed) in the range of about 1 to about 2000 nM, with preferred compounds having IC$_{50}$ values in the range of about 1 to about 100 nM.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

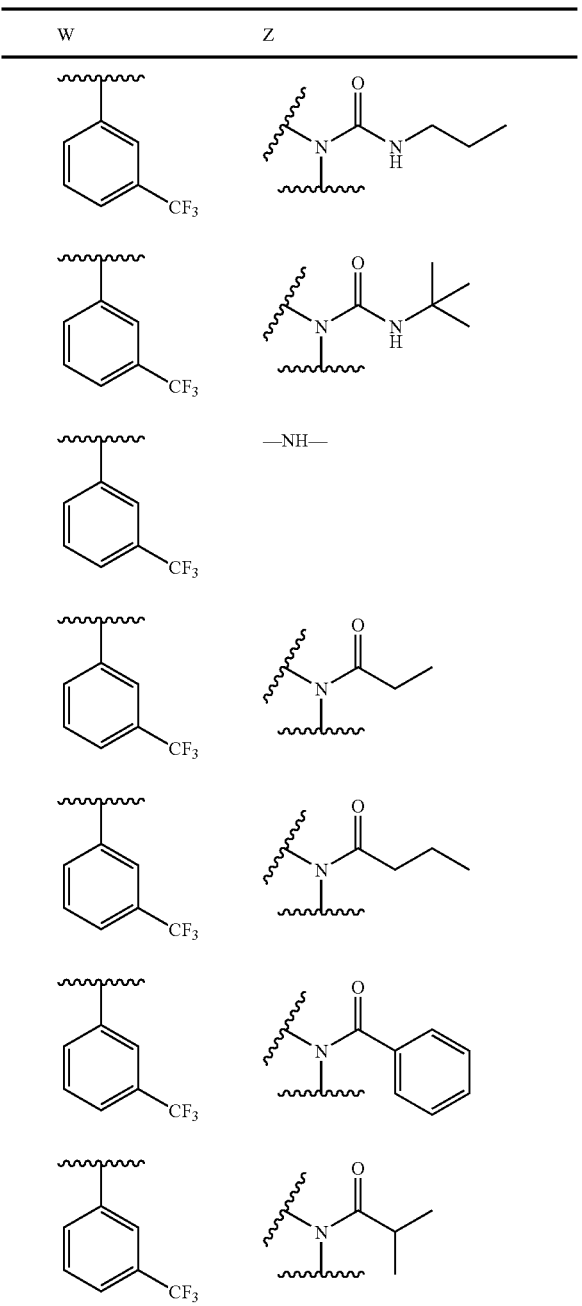
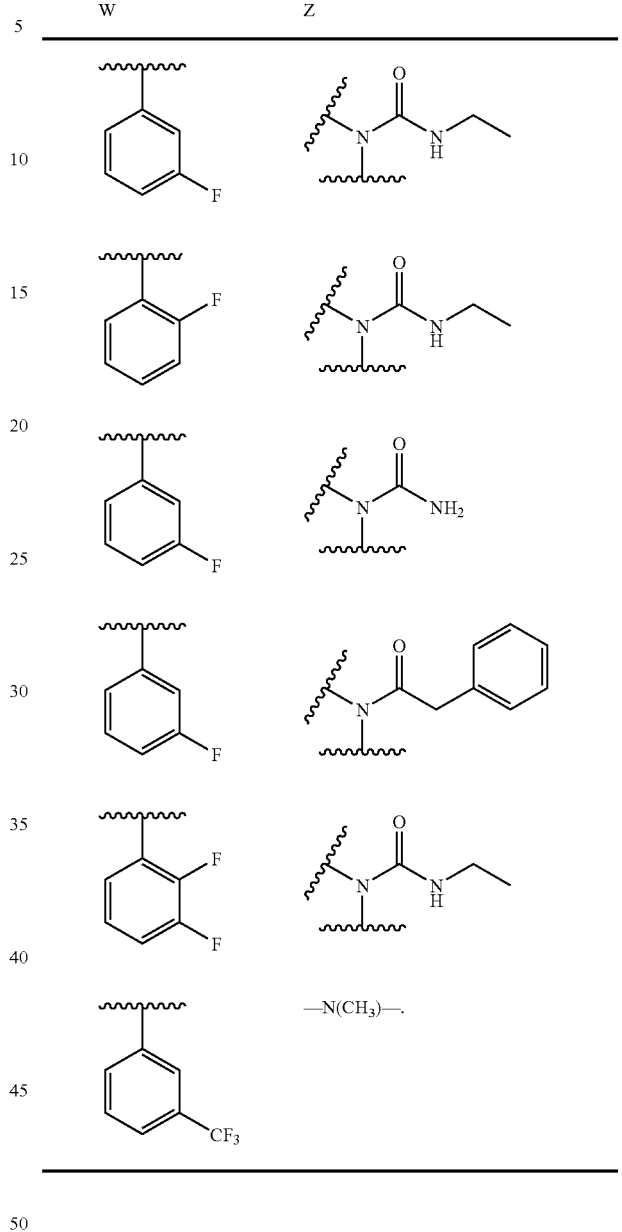

What is claimed:

1. A compound represented by the structural formula

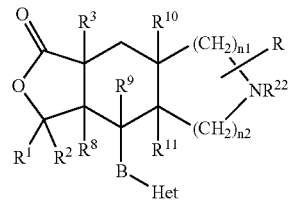

or a pharmaceutically acceptable salt thereof, wherein:

R is 1 to 3 substituents independently selected from the group consisting of H, C$_1$–C$_6$ alkyl, halogen, hydroxy, amino, (C$_1$–C$_6$)alkyl-amino, (C$_1$–C$_6$)-dialkylamino, (C$_1$–C$_6$)alkoxy, —COR$^{16}$, —COOR$^{17}$, —SOR$^{16}$, —SO$_2$R$^{16}$, —SO$_2$NR$^{17}$R$^{18}$, —NR$^{17}$SO$_2$R$^{18}$, —NR$^{16}$COR$^{16a}$, —NR$^{16}$COOR$^{16a}$, —NR$^{16}$CONR$^4$R$^5$, fluoro-(C$_1$–C$_6$)alkyl, difluoro (C$_1$–C$_6$)alkyl, trifluoro(C$_1$–C$_6$)alkyl, C$_3$–C$_6$ cycloalkyl, aryl(C$_1$–C$_6$)alkyl, hydroxy(C$_1$–C$_6$)alkyl, amino-(C$_1$–C$_6$)-alkyl, aryl and thio(C$_1$–C$_6$)alkyl;

R$^1$ and R$^2$ are independently selected from the group consisting of H, C$_1$–C$_6$ alkyl, fluoro(C$_1$–C$_6$)alkyl, difluoro(C$_1$–C$_6$)alkyl, trifluoro-(C$_1$–C$_6$)alkyl, C$_3$–C$_6$ cycloalkyl, C$_2$–C$_6$ alkenyl, aryl(C$_1$–C$_6$)alkyl, hydroxy-(C$_1$–C$_6$)alkyl, amino(C$_1$–C$_6$)alkyl, aryl and thio (C$_1$–C$_6$)alkyl;

R$^3$ is H, hydroxy, C$_1$–C$_6$alkoxy, aryloxy, aryl(C$_1$–C$_6$) alkyloxy, (C$_3$–C$_6$)cycloalkyloxy, —SOR$^{16}$, —SO$_2$R$^{17}$, —SO$_2$NR$^{18}$R$^{19}$, —SR$^{18}$, —SO$_3$H, —C(O)OR$^{17}$, —C(O)NR$^{18}$R$^{19}$, —OC(O)R$^{32}$, —OC(O)NR$^{33}$R$^{34}$, —(CR$^{33}$R$^{34}$)$_n$OR$^{32}$, —NR$^4$R$^5$, —NR$^{33}$COOR$^{32}$, —NR$^{33}$COR$^{32}$, —NR$^{33}$S(O)$_2$R$^{32}$, —NR$^{33}$CONR$^{33}$R$^{34}$, —NR$^{33}$S(O)$_2$NR$^{33}$R$^{34}$, —(CR$^{33}$R$^{34}$)$_n$NR$^4$R$^5$, —(CR$^{33}$R$^{34}$)$_n$NR$^{33}$COOR$^{32}$, —(CR$^{33}$R$^{34}$)$_n$NR$^{33}$COR$^{32}$, —(CR$^{33}$R$^{34}$)$_n$NR$^{33}$S(O)$_2$R$^{32}$, —(CR$^{33}$R$^{34}$)$_n$NR$^{33}$CONR$^{33}$R$^{34}$, —(CR$^{33}$R$^{34}$)$_n$NR$^{33}$S(O)$_2$NR$^{33}$R$^{34}$, (C$_1$–C$_6$)alkyl, halogen, C$_3$–C$_6$ cycloalkyl, C$_2$–C$_6$ alkenyl, —CN, aryl, —P(O)(OR$^7$)$_2$ or (C$_1$–C$_6$)alkyl substituted by 1 to 3 substituents independently selected from the group consisting of halogen, —OH, —NH$_2$, aryl, —COOH, —SO$_3$H, thio and (C$_1$–C$_6$)alkylthio;

n is 1, 2, 3 or 4;

n1 and n2 are independently 0–3, provided that the sum of n1 and n2 is 3;

Het is a pyridine, wherein Het is attached to B by a carbon atom ring member, and wherein the Het group is substituted by 1 to 4 substituents, W, independently selected from the group consisting of $C_1$–$C_6$ alkyl;
—$NR^4R^5$; —$NHCOR^{26}$; —$NHSO_2R^{16}$;
$R^{21}$-aryl; aryl wherein adjacent carbons form a ring with a methylenedioxy group; and
$R^{21}$-heteroaryl;

$R^4$ and $R^5$ are independently selected from the group consisting of H, $C_1$–$C_6$ alkyl, phenyl, benzyl and $C_3$–$C_6$ cycloalkyl, or $R^4$ and $R^5$ together are —($CH_2$)$_3$—, —($CH_2$)$_4$—, —($CH_2$)$_5$— or —($CH_2$)$_2$$NR^7$—($CH_2$)$_2$— and form a ring with the nitrogen to which they are attached;

$R^7$ is H or ($C_1$–$C_6$)alkyl;

$R^8$, $R^{10}$ and $R^{11}$ are independently selected from the group consisting of $R^1$ and —$OR^1$;

$R^9$ is H, OH, —$NR^4R^5$, $C_1$–$C_6$alkoxy, halogen or halo($C_1$–$C_6$)alkyl;

$R^{16}$ and $R^{16a}$ are independently selected from the group consisting of $C_1$–$C_6$ alkyl, phenyl and benzyl;

$R^{17}$, $R^{18}$ and $R^{19}$ are independently selected from the group consisting of H, $C_1$–$C_6$alkyl, phenyl and benzyl;

$R^{21}$ is 1 to 3 substituents independently selected from the group consisting of H, —$CF_3$, —$OCF_3$, halogen, —$NO_2$, —CN, $C_1$–$C_6$ alkyl, $C_1$–$C_6$ alkoxy, —$NH_2$, ($C_1$–$C_6$)-alkyl-amino, di-(($C_1$–$C_6$)alkyl)amino, amino($C_1$–$C_6$)alkyl, ($C_1$–$C_6$)-alkylamino($C_1$–$C_6$)alkyl, di-(($C_1$–$C_6$)alkyl)-amino($C_1$–$C_6$)alkyl, hydroxy-($C_1$–$C_6$)alkyl, —$COOR^{17}$, —$COR^{17}$, —$CONR^{24}R^{25}$, —$NHCOR^{16}$, —$NHSO_2R^{16}$, —$NHSO_2CH_2CF_3$, —$SO_2NR^{24}R^{25}$, —$NR^{29}C(O)NR^{24}R^{25}$, —$SO_2R^{30}$, —$P(O)(OR^{29})_2$, aryl, aryl($C_1$–$C_6$)alkyl, and —$CR^{29}$(=$NOR^{28}$);

$R^{22}$ is —$COR^{23}$, —$S(O)R^{31}$, —$S(O)_2R^{31}$, —$SO_2NR^{24}R^{25}$ or —$COOR^{27}$;

$R^{23}$ is halo($C_1$–$C_6$)alkyl; $C_2$–$C_6$ alkenyl; halo($C_2$–$C_6$)alkenyl; $C_2$–$C_6$ alkynyl; $C_3$–$C_7$-cycloalkyl; ($C_3$–$C_7$)cycloalkyl($C_1$–$C_6$)alkyl; ($C_3$–$C_7$)cycloalkyl substituted by 1 to 3 substituents selected from the group consisting of halo, ($C_1$–$C_3$)alkoxy($C_1$–$C_3$)alkyl, hydroxy and $C_1$–$C_6$ alkoxy; aryl; aryl($C_2$–$C_6$)alkyl; heteroaryl; heterocycloalkyl; ($C_1$–$C_6$)alkyl substituted by 1–3 substituents independently selected from —COOH and —$SO_3H$; or

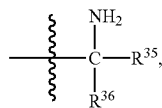

wherein $R^{35}$ and $R^{36}$ are independently selected from the group consisting of H, alkyl, or $R^{37}$-substituted $C_1$–$C_6$ alkyl, wherein $R^{37}$ is selected from the group consisting of HO—, HS—, $CH_3S$—, —$NH_2$, phenyl, p-hydroxyphenyl and indolyl;

$R^{24}$ and $R^{25}$ are independently selected form the group consisting of H, $C_1$–$C_6$ alkyl, halo($C_1$–$C_6$)alkyl, $C_2$–$C_6$ alkenyl, halo($C_2$–$C_6$)alkenyl, $C_2$–$C_6$ alkynyl, aryl, aryl-($C_1$–$C_6$)alkyl, $C_3$–$C_7$-cycloalkyl, halo($C_3$–$C_7$)cycloalkyl, ($C_1$–$C_3$)alkoxy($C_1$–$C_3$)-alkyl, hydroxy and $C_1$–$C_6$ alkoxy;

$R^{26}$ is $C_3$–$C_7$-cycloalkyl, aryl, aryl-($C_1$–$C_6$)alkyl, heteroaryl, heteroaryl-($C_1$–$C_6$)alkyl or ($C_1$–$C_6$)alkylamino;

$R^{27}$ is $C_1$–$C_6$alkyl, phenyl, benzyl, ($C_1$–$C_3$)alkoxy($C_1$–$C_3$)-alkyl, ($C_3$–$C_7$)-cycloalkyl, carboxy($C_1$–$C_6$) alkyl, sulfo($C_1$–$C_6$)alkyl, or ($C_1$–$C_6$)alkyl substituted by $NR^{18}R^{19}$ and carboxy;

$R^{28}$ is H, $C_1$–$C_6$ alkyl, phenyl, benzyl or ($C_1$–$C_3$)alkoxy($C_1$–$C_3$)alkyl;

$R^{29}$ and $R^{30}$ are independently selected from the group consisting of H and $C_1$–$C_6$ alkyl;

$R^{31}$ is ($C_1$–$C_6$)alkyl; halo($C_1$–$C_6$)alkyl; $C_2$–$C_6$ alkenyl; halo($C_2$–$C_6$)alkyl; $C_2$–$C_6$ alkynyl; $C_3$–$C_7$-cycloalkyl; ($C_3$–$C_7$)cycloalkyl substituted by 1 to 3 substituents selected from the group consisting of halo, ($C_1$–$C_3$) alkoxy($C_1$–$C_3$)alkyl, hydroxy and $C_1$–$C_6$ alkoxy; aryl; aryl($C_1$–$C_6$)alkyl; heteroaryl; heterocycloalkyl; ($C_1$–$C_6$)alkyl substituted by 1–3 substituents independently selected from —COOH and —$SO_3H$; or ($C_1$–$C_6$)alkoxy;

$R^{32}$ is $R^{35}$—($C_1$–$C_6$)alkyl, $R^{35}$—($C_3$–$C_7$)cycloalkyl, $R^{35}$—($C_2$–$C_6$)alkenyl, $R^{35}$—($C_2$–$C_6$)-alkynyl or $R^{35}$-aryl, wherein $R^{35}$ is 1 or 2 substituents independently selected from the group consisting of H, —COOH, —$NH_2$, —$SO_3H$, =O and =$NOR^{28}$; and $R^{33}$ and $R^{34}$ are independently selected from the group consisting of H, ($C_1$–$C_6$)alkyl and $C_3$–$C_7$-cycloalkyl.

2. A compound of claim 1 wherein $R^1$, $R^{10}$ and $R^{11}$ are independently selected from the group consisting of H and $C_1$–$C_6$ alkyl; $R^2$ and $R^8$ are each hydrogen; and $R^9$ is H, OH or $C_1$–$C_6$ alkoxy.

3. A compound of claim 1 wherein R is H, halogen, OH, $C_1$–$C_6$ alkyl, $C_1$–$C_6$ alkoxy or amino.

4. A compound of claim 1 wherein B is —CH=CH—.

5. A compound of claim 1 wherein W is —$NR^4R^5$, —$NHCOR^{26}$, —$NHSO_2R^{16}$, $R^{21}$-aryl or heteroaryl.

6. A compound of claim 5 wherein $R^{21}$ is 1 to 3 substituents independently selected from the group consisting of H, —$CF_3$, —$OCF_3$, halogen, —CN, $C_1$–$C_6$ alkyl, $C_1$–$C_6$ alkoxy, —$NH_2$ and —$CR^{29}$(=$NOR^{28}$).

7. A compound of claim 1 wherein $R^3$ is H, hydroxy, $C_1$–$C_6$ alkoxy, halogen, $C_3$–$C_6$ cycloalkyl, —CN, ($C_1$–$C_6$)alkyl, —$COOR^{17}$ or —$NR^4R^5$.

8. A compound of claim 1 wherein $R^{22}$ is —$COR^{23}$, —$S(O)_2R^{31}$ or —$COOR^{27}$.

9. A compound of claim 8 wherein $R^{23}$ is $C_3$–$C_7$-cycloalkyl; ($C_3$–$C_7$)cycloalkyl substituted by 1 to 3 substituents selected from the group consisting of halo, ($C_1$–$C_3$) alkoxy($C_1$–$C_3$)alkyl, hydroxy and $C_1$–$C_6$ alkoxy; ($C_3$–$C_7$) cycloalkyl($C_1$–$C_6$)alkyl; aryl; or aryl($C_2$–$C_6$)alkyl.

10. A compound of claim 9 wherein $R^{23}$ is $C_3$–$C_7$-cycloalkyl; ($C_3$–$C_7$)cycloalkyl($C_1$–$C_6$)alkyl or aryl-($C_2$–$C_6$) alkyl.

11. A compound of claim 8 wherein $R^{31}$ is ($C_1$–$C_6$)alkyl, $C_3$–$C_7$-cycloalkyl, aryl or aryl($C_1$–$C_6$)alkyl.

12. A compound of claim 8 wherein $R^{27}$ is $C_1$–$C_6$alkyl, phenyl, benzyl, ($C_1$–$C_3$)alkoxy($C_1$–$C_3$)alkyl or ($C_3$–$C_7$) cycloalkyl.

13. A compound of claim 1 selected from the group consisting of compounds of the formula

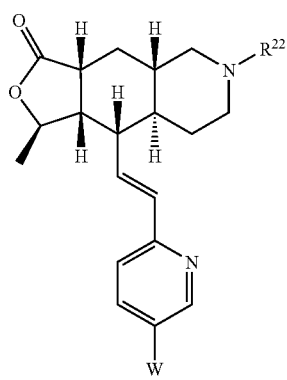

wherein W and R²² are as defined in the table:

| W | R²² |
|---|---|
| 3-CF₃-phenyl | —CO₂Et |
| 3-F-phenyl | —CO₂Et |
| 2-F-phenyl | —CO₂Et |
| 2,3-diF-phenyl | —CO₂Et |
| 3-CF₃-phenyl | —C(O)-cyclopropyl |
| 3-CF₃-phenyl | —S(O)₂CH₃ |
| 3-CF₃-phenyl | —S(O)₂Et |
| 3-CF₃-phenyl | —C(O)OCH₂-phenyl |
| 3-CF₃-phenyl | —C(O)CH₂-cyclopropyl |
| 3-F-phenyl | —C(O)-cyclopropyl |
| 3-F-phenyl | —S(O)₂CH₃ |
| 2-F-phenyl | —C(O)-cyclopropyl |
| 2-F-phenyl | —S(O)₂CH₃ |
| 2,3-diF-phenyl | —C(O)-cyclopropyl |
| 3-CN-phenyl | —CO₂Et |
| 3-thienyl | —CO₂Et |

-continued

| W | R²² |
|---|---|
| (m-phenyl with N-OH acetyl group) | —CO₂Et |
| (m-phenyl with N-OEt acetyl group) | —CO₂Et |
| (2-pyridyl) | —CO₂Et |
| (m-fluorophenyl) | —CO₂CH₂CH₂OMe | and compounds of the formula

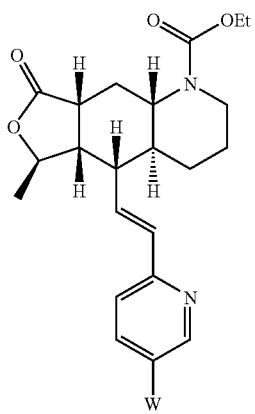

wherein W is as defined in the following table:

| W |
|---|
| (2-fluorophenyl) |
| (3-fluorophenyl) |
| (3-cyanophenyl) |

14. A pharmaceutical composition comprising an effective amount of at least one compound of claim 1 and a pharmaceutically acceptable carrier.

15. A compound selected from the group consisting of compounds of the formula wherein W and Z are as defined in the following table:

| W | Z |
|---|---|
| (3-CF₃-phenyl) | (N-acetyl) |
| (3-CF₃-phenyl) | (N-ethylurea) |
| (3-CF₃-phenyl) | (N-isopropylurea) |